United States Patent
Tochilnik

(10) Patent No.: US 10,437,877 B2
(45) Date of Patent: *Oct. 8, 2019

(54) USER-CONFIGURABLE RADIOLOGICAL DATA TRANSFORMATION, INTEGRATION, ROUTING AND ARCHIVING ENGINE

(71) Applicant: Dicom Systems, Inc., Campbell, CA (US)

(72) Inventor: Dmitriy Tochilnik, Campbell, CA (US)

(73) Assignee: Dicom Systems, Inc., Campbell, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/493,105

(22) Filed: Apr. 20, 2017

(65) Prior Publication Data

US 2017/0287093 A1 Oct. 5, 2017

Related U.S. Application Data

(63) Continuation-in-part of application No. 15/183,597, filed on Jun. 15, 2016, now abandoned, which is a
(Continued)

(51) Int. Cl.
| | |
|---|---|
| *G06F 16/51* | (2019.01) |
| *G06F 19/00* | (2018.01) |
| *G16H 40/20* | (2018.01) |
| *G06F 16/26* | (2019.01) |
| *G16H 40/63* | (2018.01) |
| *G16H 30/40* | (2018.01) |
| *G16H 30/20* | (2018.01) |

(Continued)

(52) U.S. Cl.
CPC ............ *G06F 16/51* (2019.01); *G06F 16/113* (2019.01); *G06F 16/116* (2019.01); *G06F 16/26* (2019.01); *G06F 19/321* (2013.01); *G06F 19/324* (2013.01); *G16H 10/60* (2018.01); *G16H 30/20* (2018.01); *G16H 30/40* (2018.01); *G16H 40/20* (2018.01); *G16H 40/63* (2018.01); *G16H 40/40* (2018.01)

(58) Field of Classification Search
CPC combination set(s) only.
See application file for complete search history.

(56) References Cited

U.S. PATENT DOCUMENTS

| | | |
|---|---|---|
| 4,407,294 A | 10/1983 | Vilkomerson |
| 4,575,625 A | 3/1986 | Knowles |

(Continued)

OTHER PUBLICATIONS

Eichelberg et al., "A survey and analysis of electronic healthcare record standards," Acm Computing Surveys, 37 (4):277-315 (2005).
(Continued)

*Primary Examiner* — Farhan M Syed
(74) *Attorney, Agent, or Firm* — Sheppard Mullin Richter & Hampton LLP

(57) ABSTRACT

A user-configurable radiological data transformation, routing and archiving engine includes a plurality of sub-engines representing algorithms programmed to be processed by a processor, the sub-engines including a user-configurable transformation sub-engine, a user-configurable routing sub-engine, a user-configurable archiving sub-engine and a user-configurable priors puller sub-engine.

20 Claims, 51 Drawing Sheets

Related U.S. Application Data continuation of application No. 13/385,509, filed on Feb. 21, 2012, now Pat. No. 9,390,153.

(51) Int. Cl.
  *G16H 10/60* (2018.01)
  *G06F 16/11* (2019.01)
  *G16H 40/40* (2018.01)

(56) References Cited

U.S. PATENT DOCUMENTS

| | | | |
|---|---|---|---|
| 5,002,561 A | 3/1991 | Fisher | |
| 5,220,175 A | 6/1993 | Taaffe et al. | |
| 5,237,714 A | 8/1993 | Baron | |
| 5,253,653 A | 10/1993 | Daigle et al. | |
| 5,325,851 A | 7/1994 | Reynolds et al. | |
| 5,326,532 A | 7/1994 | Taylor | |
| 5,394,455 A | 2/1995 | Roeck et al. | |
| 5,426,582 A | 6/1995 | Bossaert et al. | |
| 5,452,416 A | 9/1995 | Hilton et al. | |
| 5,487,290 A | 1/1996 | Miller et al. | |
| 5,564,085 A | 10/1996 | Chen et al. | |
| 5,592,237 A | 1/1997 | Greenway et al. | |
| 5,653,135 A | 8/1997 | Miller et al. | |
| 5,715,716 A | 2/1998 | Miller et al. | |
| 5,720,194 A | 2/1998 | Miller et al. | |
| 5,740,267 A | 4/1998 | Echerer et al. | |
| 5,805,118 A | 9/1998 | Mishra et al. | |
| 5,807,321 A | 9/1998 | Stoker et al. | |
| 5,960,655 A | 10/1999 | Miller et al. | |
| 6,081,267 A | 6/2000 | Stockham et al. | |
| 6,210,788 B1 | 4/2001 | Cuypers | |
| 6,696,973 B1 | 2/2004 | Ritter et al. | |
| 6,701,343 B1 | 3/2004 | Kenyon | |
| 6,751,347 B2 | 6/2004 | Pettigrew et al. | |
| 6,757,425 B2 | 6/2004 | Pettigrew et al. | |
| 6,898,309 B2 | 5/2005 | Pettigrew et al. | |
| 7,219,332 B2 | 5/2007 | Gouge et al. | |
| 7,444,390 B2 | 10/2008 | Tadayon et al. | |
| 7,624,277 B1 | 11/2009 | Simard et al. | |
| 7,630,371 B2 * | 12/2009 | Hernandez | G06Q 10/10 370/392 |
| 7,865,358 B2 | 1/2011 | Green et al. | |
| 7,899,683 B2 * | 3/2011 | Schoenberg | G06F 19/322 600/300 |
| 7,930,636 B2 | 4/2011 | Garbow et al. | |
| 7,962,908 B2 | 6/2011 | Gouge et al. | |
| 8,000,977 B2 * | 8/2011 | Achan | G06Q 10/103 705/2 |
| 8,108,648 B2 | 1/2012 | Srinivasan et al. | |
| 8,446,463 B2 | 5/2013 | Fleming et al. | |
| 2001/0028735 A1 | 10/2001 | Pettigrew et al. | |
| 2001/0028736 A1 | 10/2001 | Pettigrew et al. | |
| 2001/0028738 A1 | 10/2001 | Pettigrew et al. | |
| 2002/0104069 A1 | 8/2002 | Gouge et al. | |
| 2005/0165623 A1 * | 7/2005 | Landi | G06F 21/6254 705/2 |
| 2006/0052945 A1 * | 3/2006 | Rabinowitz | G16B 40/00 702/20 |
| 2007/0064703 A1 * | 3/2007 | Hernandez | G06Q 10/10 370/392 |
| 2007/0143215 A1 * | 6/2007 | Willems | G16H 10/65 705/51 |
| 2007/0173702 A1 * | 7/2007 | Dlugos | G06F 19/3481 600/300 |
| 2008/0046292 A1 * | 2/2008 | Myers | G06Q 50/24 705/3 |
| 2008/0288280 A1 * | 11/2008 | Belcher | G06F 19/328 705/2 |
| 2009/0063995 A1 | 3/2009 | Baron et al. | |
| 2009/0064000 A1 | 3/2009 | Garbow et al. | |
| 2009/0132963 A1 | 5/2009 | Morita et al. | |
| 2010/0115288 A1 * | 5/2010 | Monk | G06F 21/602 713/189 |
| 2011/0119599 A1 | 5/2011 | Klassen et al. | |
| 2011/0295873 A1 * | 12/2011 | Potter | G06F 19/321 707/769 |
| 2012/0046972 A1 * | 2/2012 | Tonti | G06F 19/321 705/3 |
| 2012/0070045 A1 * | 3/2012 | Vesper | G06Q 50/22 382/128 |
| 2012/0180071 A1 | 7/2012 | Lesandro et al. | |
| 2012/0323593 A1 * | 12/2012 | Backhaus | G06F 19/321 705/2 |
| 2013/0060579 A1 * | 3/2013 | Yu | G06Q 10/06 705/3 |

OTHER PUBLICATIONS

Kimura et al., "MERIT-9: a patient information exchange guideline using MML, HL7 and DICOM," International Journal of Medical Informatics, 51(1):59-68 (1998).

Corepoint Health, Corepoint Integration Engine, pp. 1-28 (2009).

* cited by examiner

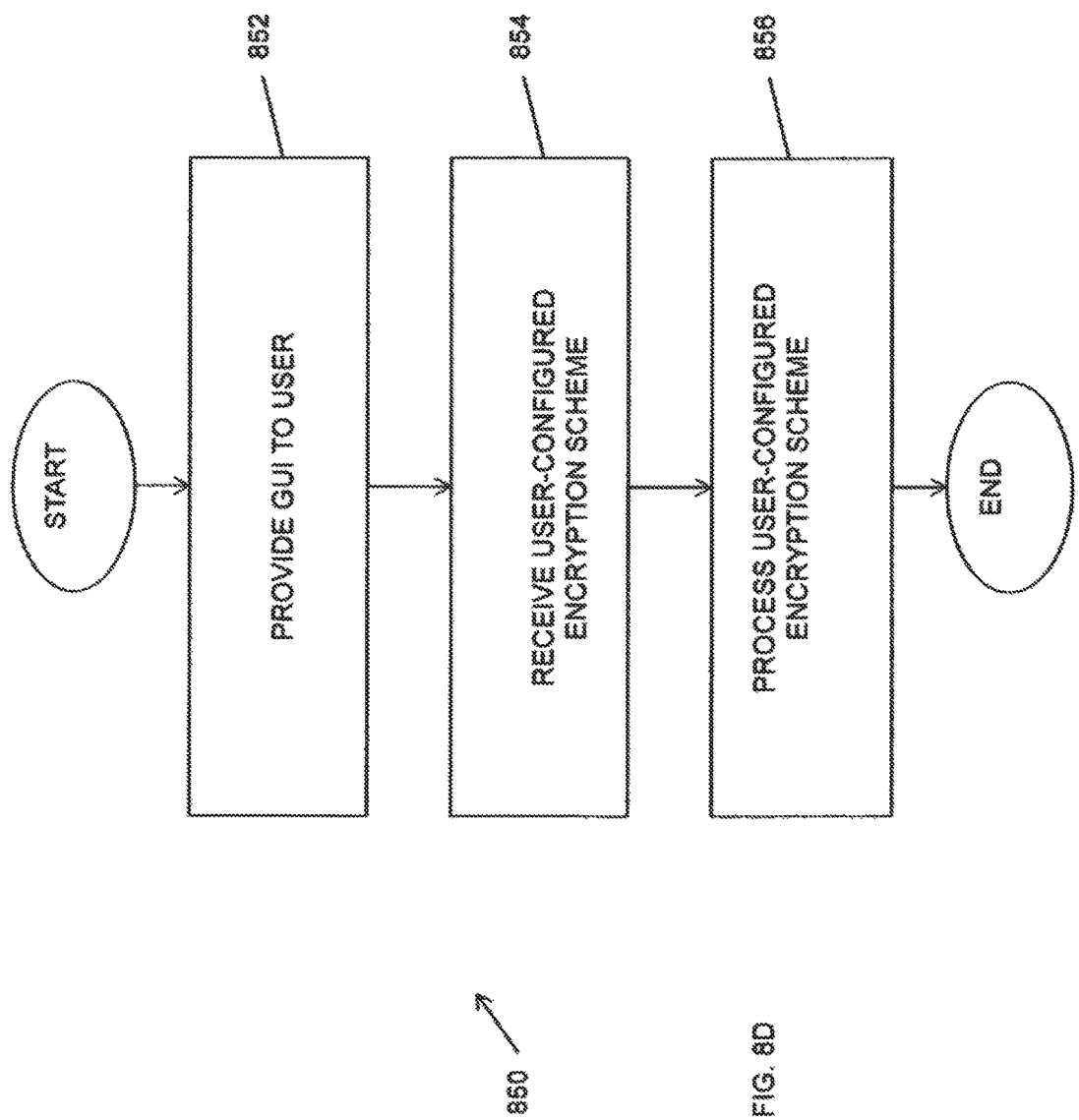

Script Editor

▼ User libraries — 1010
h17_create11
string.random
anonymizer

1020

```
  anonymizer
1  require ("string.random")
2  -- Dicom Systems demo anonymizer, copyright 2010
3  function DcmAnonymize (dcm)
4    local studyUid = dcm : get ("StudyInstanceUID")
5
6    local newpn = "ANON^ANON"
7    local newid = "ID000000"
8    local newaccnum = "A000000"
9    local newsuid = nil
10
11   if studyUid == nil then
12     local mem = memcache(studyUid, 60*60)
13
14     newpn = mem["newpn"]
15     if newpn == nil then
16       newpn = string.random(6 "ABCDEFGH")..""
17     string.random(5, "0123456789")
18     mem["newpn"] = newpn
19   end
20   newpid = mem["newpid"]
21   if newpid == nil then
22     newpid = "A" string.random(6 "0123456789")
```

1000

• Dcmsys examples
• Dicom scripting reference manual
• HL7 scripting reference manual Input
[HL7] [Dicom]

Output
[Output] [HL7] [Dicom]

[Run script] [Save] [Save as library] [Close]

Route

Source device:
☑ AETitle: boxanon    Host: *  ⟵ 2010

Local device:
☑ AETitle: boxasec    Port: 1043 ⟵ 2012

Route to:
☑ AETitle: TESTDOWN   Host: 172.16.1.230   Port: 1041 ⟵ 2014

Failover destination:
☑ AETitle: _____    Host: _____   Port: _____ ⟵ 2016

Enabled: ☑ True ⟵ 2018

Priority: 99 ⟵ 2020

Route conditions: ⟵ 2030

```
(((0008,0090) opLike Mackenzie)
or (((0008,0090) opLike Douglas Macke
)
and (((0008,0060) opEquality CT)
or (((0008,0060) opEquality CR)
```

[And ▾] [Equal ▾]

The conditional expression syntax is va
(((0008,0090) opLike Mackenzie) or ((
) and (((0008,0060) opEquality CT) or ((  ⟵ 2040

2000

Select AETitle ⟵ 2100

Filter: _____

Any AETitle
boxanon:*:2010
boxasec:*:1043
boxa:*:1040
AETITLE:69.110.4.130:999
TESTDOWN:172.16.1.230:1041
boxbsec:172.16.1.229:1043
boxb:70.20.124.23:1040
dcmflow:172.16.0.30:104

[Save] [Cancel]

HL7 Workflow

Event Name: INCOMING-DICOM-STUDY — 3210

Event description: [                    ] — 3220

Enabled: DCMSYS ENGINE — 3230

Tasks: True — 3240

Click here to add new ....

— 3250 Dicom Condition    [✓] + ×

— 3260 Build HL7 Message  [✓] + ×

— 3270 Route HL7 Message  [✓] − ×

Host: 10.10.10.24

Port: 1051

[Save]  [Hide]

[Save]  [Cancel]

Show All  Hide All

HL7 Workflow

② Event Name: [request_patient_id] — 3210

② Event description: [REQUEST PATIENT ID from TAD] — 3220

② Enabled: [True ▼] — 3230

② Tasks: ✓ Click here to add new — 3500
  HL7 Condition
  HL7 Transformation
  Route HL7 Message
  Send HL7 Message
  Build Worklist entry
  Export to CSV file
  Build HL7 Message
  Return HL7 Message
  Priors Request
  Submit document to the XDS Repository Service
  Excute Script
  Build Dicom object
  Dicom Condition 3260 — ② Build
Create HL...

3270 — ② Build
Send HL7...

Show All  Hide All

[☐ — ×]
[☐ — ×]

3200

[Save] [Cancel]

FIG. 35

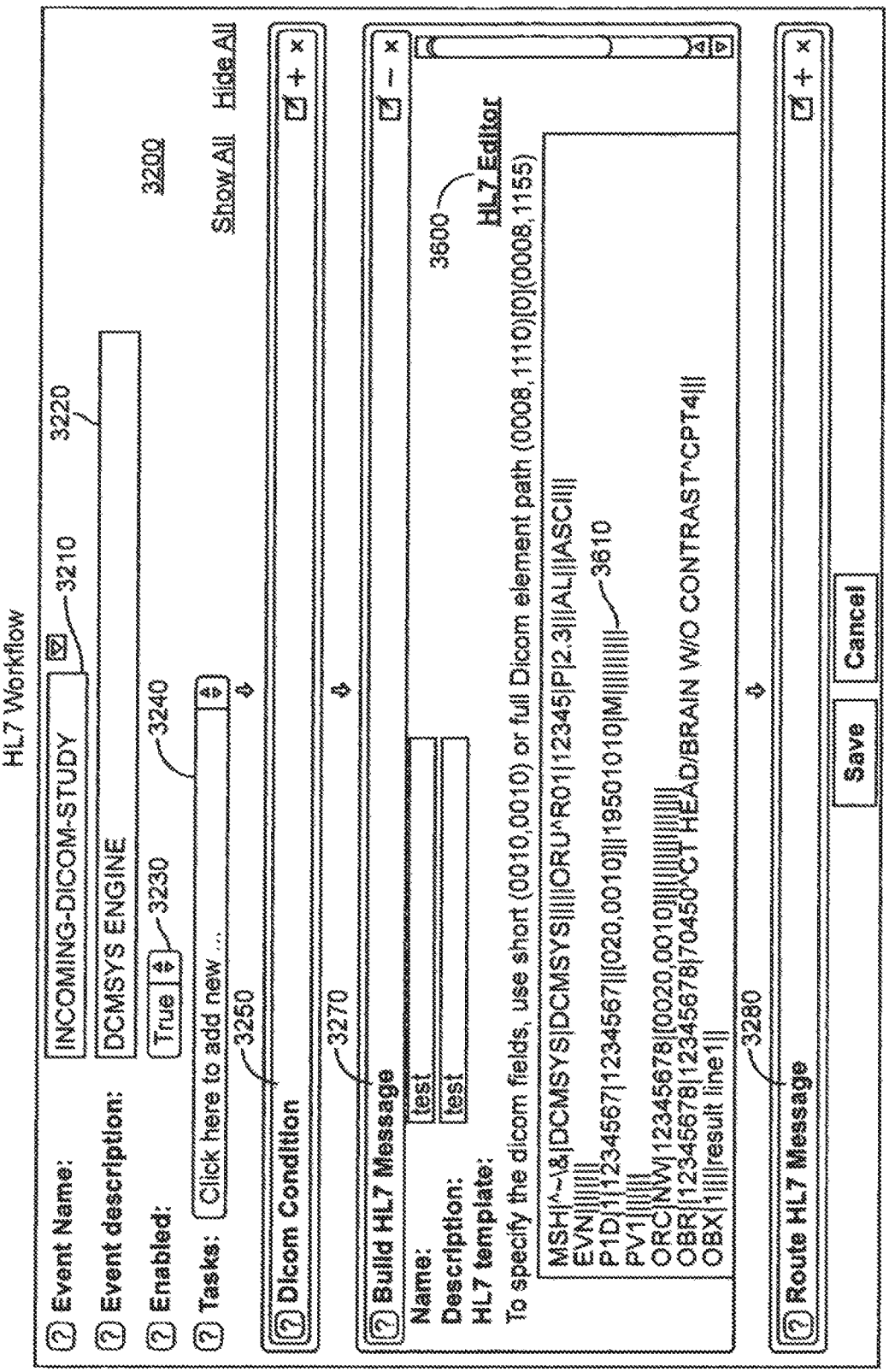

| | |
|---|---|
| Remote AETitle | |
| ⓘ AETitle: | _____ 3810 |
| ⓘ Host: | _____ |
| ⓘ Port: | _____ |
| ⓘ Enabled: | True |
| ⓘ Connection Secure Mode: | Nonsecure — 3820 |
| ⓘ Local Certificate: | RSNA 2011 — 3830 |
| ⓘ Remote Trusted Certificates: | RSNA 2011 — 3840 |
| ⓘ TLS Access mode: | Allow any certificate — 3850 |
| ⓘ Remote Local AE: | |
| ⓘ PDU optimization: | Mode: Default  Size: 131072 — 3800 |
| ⓘ Network optimization: | LAN |
| ⓘ Connection timeout: | 0   0 - use default timeout (60 sec) |
| ⓘ Check Connection: | No |
| ⓘ Max Concurrent Connections: | 0 - unlimited |
| ⓘ Description: | |
| ⓘ Grouping key: | |
| ⓘ Allowed Incoming Syntaxes: | Auto — 3860 |
| ⓘ Preferred Outgoing Syntaxes: | Auto — 3870 |
| ⓘ Bit preserving mode: | False |
| ⓘ Accept Unknown SOP Classes: | False |
| ⓘ Storage Commit Mode: | Disable |
| ⓘ Send MPPS: | Never |

FIG. 38

| | | |
|---|---|---|
| AETitle: | | ― 3810 |
| Host: | | |
| Port: | | |
| Enabled: | True | |
| Connection Secure Mode: | Anonymous certificate | 3900 |
| Local Certificate: | RSNA 2010 Demo Box A | |
| Remote Trusted Certificates: | ✓ RSNA 2011 BAYLOR | |
| TLS Access mode: | Allow any certificate | ― 3850 |
| Remote Local AE: | | 3840 |
| PDU optimization: | Mode: Default Size: 131072 | |
| Network optimization: | LAN | 3800 |
| Connection timeout | 0    0 - use default timeout (60 sec) | |
| Check Connection | No | |
| Max Concurrent Connections | 0 - unlimited | |
| Description: | | |
| Grouping key: | | |
| Allowed Incoming Syntaxes | Auto | ― 3860 |
| Preferred Outgoing Syntaxes | Auto | ― 3870 |
| Bit preserving mode | False | |
| Accept Unknown SOP Classes: | False | |
| Storage Commit Mode: | Disable | |
| Send MPPS: | Never | |

Remote AETitle

FIG. 39

SOP Class Configuration

SOP Class Tree — Check All  Uncheck All

- ☑ Storage*(84/84 checked)*
- ☑ Worklist and Query/Retrieve*(11/11 checked)*
- ☑ Storage Commitment*(1/1 checked)*
- ☑ MPPS*(3/3 checked)*
- ☑ Verification*(1/1 checked)*
- ☑ Instance Availability Notification*(1/1 checked)*
- ☑ Media Creation Management*(1/1 checked)*
- ☑ SOP Class Relationship Negotiation*(1/1 checked)*
- ☑ UTC Synchronization Frame of Reference (CP 432)*(1/1 checked)*
- ☑ Hanging Protocols*(3/3 checked)*

Enabled transfer syntaxes for [Group: Storage] — Check All  Uncheck All

| | | |
|---|---|---|
| ☑ 1.2.840.10008.1.2.4.90 | JPEG 2000 (Lossless only) | |
| ☑ 1.2.840.10008.1.2.4.91 | JPEG 2000 (Lossless or Lossy) | |
| ☑ 1.2.840.10008.1.2.4.92 | JPEG 2000 Part 2 Multicomponent Image Compression (Lossless only) | 4200 |
| ☑ 1.2.840.10008.1.2.4.93 | JPEG 2000 Part 2 Multicomponent Image Compression (Lossless or Lossy) | |
| ☑ 1.2.840.10008.1.2.4.50 | JPEG Baseline | |
| ☑ 1.2.840.10008.1.2.4.51 | JPEG Extended, Process 2+4 | |
| ☑ 1.2.840.10008.1.2.4.52 | JPEG Extended, Process 3+5 | |
| ☑ 1.2.840.10008.1.2.4.53 | JPEG Spectral Selection, Non-hierarchical, Process 6+8 | |
| ☑ 1.2.840.10008.1.2.4.54 | JPEG Spectral Selection, Non-hierarchical, Process 7+9 | |
| ☑ 1.2.840.10008.1.2.4.55 | JPEG Full Progression, Non-hierarchical, Process 10+12 | |

[Save] [Cancel]

FIG. 42

SOP Class Configuration

SOP Class Tree — Check All / Uncheck All

- ☑ Storage(84/84 checked)
- ☑ Worklist and Query/Retrieve(11/11 checked)
- ☑ Storage Commitment(1/1 checked)
- ☑ MPPS(3/3 checked)
- ☑ Verification(1/1 checked)
- ☑ Instance Availability Notification(1/1 checked)
- ☑ Media Creation Management(1/1 checked)
- ☑ SOP Class Relationship Negotiation(1/1 checked)
- ☑ UTC Synchronization Frame of Reference (CP 432)(1/1 checked)
- ☑ Hanging Protocols(3/3 checked)

Enabled transfer syntaxes for [Group: Storage] — Check All / Uncheck All

| | UID | Transfer Syntax |
|---|---|---|
| ☑ | 1.2.840.10008.1.2.4.50 | JPEG Baseline |
| ☑ | 1.2.840.10008.1.2.4.51 | JPEG Extended, Process 2+4 |
| ☑ | 1.2.840.10008.1.2.4.52 | JPEG Extended, Process 3+5 |
| ☑ | 1.2.840.10008.1.2.4.53 | JPEG Spectral Selection, Non-hierarchical, Process 6+8 |
| ☑ | 1.2.840.10008.1.2.4.54 | JPEG Spectral Selection, Non-hierarchical, Process 7+9 |
| ☑ | 1.2.840.10008.1.2.4.55 | JPEG Full Progression, Non-hierarchical, Process 10+12 — 4200 |
| ☑ | 1.2.840.10008.1.2.4.56 | JPEG Full Progression, Non-hierarchical, Process 11+13 |
| ☑ | 1.2.840.10008.1.2.4.57 | JPEG Lossless, Non-hierarchical, Process 14 |
| ☑ | 1.2.840.10008.1.2.4.58 | JPEG Lossless, Non-hierarchical, Process 15 |
| ☑ | 1.2.840.10008.1.2.4.59 | JPEG Extended, Hierarchical, Process 16+18 |

[Save] [Cancel]

FIG. 43

SOP Class Configuration

SOP Class Tree  Check All  Uncheck All

- ☑ Storage*(84/94 checked)*
- ☑ Worklist and Query/Retrieve*(11/11 checked)*
- ☑ Storage Commitment*(1/1 checked)*
- ☑ MPPS*(3/3 checked)*
- ☑ Verification*(1/1 checked)*
- ☑ Instance Availability Notification*(1/1 checked)*
- ☑ Media Creation Management*(1/1 checked)*
- ☑ SOP Class Relationship Negotiation*(1/1 checked)*
- ☑ UTC Synchronization Frame of Reference (CP 432)*(1/1 checked)*
- ☑ Hanging Protocols*(3/3 checked)*

Enabled transfer syntaxes for [Group: Storage]  Check All  Uncheck All

| | | |
|---|---|---|
| ☑ 1.2.840.10008.1.2.4.59 | JPEG Extended, Hierarchical, Process 16+18 | |
| ☑ 1.2.840.10008.1.2.4.60 | JPEG Extended, Hierarchical, Process 17+19 | |
| ☑ 1.2.840.10008.1.2.4.61 | JPEG Spectral Selection, Hierarchical, Process 20+22 | |
| ☑ 1.2.840.10008.1.2.4.62 | JPEG Spectral Selection, Hierarchical, Process 21+23 | |
| ☑ 1.2.840.10008.1.2.4.63 | JPEG Full Progression, Hierarchical, Process 24+26 | |
| ☑ 1.2.840.10008.1.2.4.64 | JPEG Full Progression, Hierarchical, Process 25+27 | 4200 |
| ☑ 1.2.840.10008.1.2.4.65 | JPEG Lossless, Hierarchical, Process 28 | |
| ☑ 1.2.840.10008.1.2.4.66 | JPEG Lossless, Hierarchical, Process 29 | |
| ☑ 1.2.840.10008.1.2.4.70 | JPEG Lossless, Non-hierarchical, 1st Order Prediction | |
| ☑ 1.2.840.10008.1.2.4.80 | JPEG-LS Lossless | |

[Save] [Cancel]

FIG. 44

SOP Class Configuration

SOP Class Tree      Check All    Uncheck All

- ☑ Storage(84/84 checked)
- ☑ Worklist and Query/Retrieve(11/11 checked)
- ☑ Storage Commitment(1/1 checked)
- ☑ MPPS(3/3 checked)
- ☑ Verification(1/1 checked)
- ☑ Instance Availability Notification(1/1 checked)
- ☑ Media Creation Management(1/1 checked)
- ☑ SOP Class Relationship Negotiation(1/1 checked)
- ☑ UTC Synchronization Frame of Reference (CP 432)(1/1 checked)
- ☑ Hanging Protocols(3/3 checked)

Enabled transfer syntaxes for [Group: Storage]      Check All    Uncheck All

| | | |
|---|---|---|
| ☑ 1.2.840.10008.1.2.4.70 | JPEG Lossless, Non-hierarchical, 1st Order Prediction | |
| ☑ 1.2.840.10008.1.2.4.80 | JPEG-LS Lossless | |
| ☑ 1.2.840.10008.1.2.4.81 | JPEG-LS Lossy (Near-lossless) | |
| ☑ 1.2.840.10008.1.2.5 | RLE Lossless | |
| ☑ 1.2.840.10008.1.2.4.100 | MPEG2 Main Profile @ Main Level | |
| ☑ 1.2.840.10008.1.2.1.99 | Deflated Explicit VR Little Endian | 4200 |
| ☑ 1.2.840.10008.1.2.1 | Little Endian Explicit | |
| ☑ 1.2.840.10008.1.2.2 | Big Endian Explicit | |
| ☑ 1.2.840.10008.1.2 | Little Endian Explicit | |

[Save] [Cancel]

FIG. 45

USER-CONFIGURABLE RADIOLOGICAL DATA TRANSFORMATION, INTEGRATION, ROUTING AND ARCHIVING ENGINE

CROSS-REFERENCE TO RELATED APPLICATIONS

This application is a continuation-in-part of U.S. patent application Ser. No. 15/183,597, filed on Jun. 15, 2016, which is a continuation of U.S. patent application Ser. No. 13/385,509, filed on Feb. 21, 2012, the contents of which are incorporated herein in their entirety.

TECHNICAL FIELD

The disclosed technology relates generally to data processing and more particularly to a user-configurable radiological data transformation, routing, proxying, integration, and archiving engine.

BACKGROUND

With technological advances in modern medicine, digital imaging data processing has become integral in diagnostic and research efforts. Digital imaging is used in many fields of medicine and encompasses a large number of medical imaging modalities (e.g., computed tomography, magnetic resonance, ultrasound, positron emission tomography and digital radiography). Until relatively recently, manufacturers of imaging devices and technology used proprietary image format and communication protocols. Digital Imaging and Communications in Medicine ("DICOM") created a standard for radiology imaging and communication. Since then, DICOM has dominated the field of radiology imaging and all major manufacturers conform to this standard. The DICOM standard has two major areas of focus: the data format and the communication/message protocol to exchange DICOM objects. Recently, DICOMWEB, a web standard for radiological imaging and communication, has been introduced and become the standard way to enable access to DICOM objects over the Internet.

Medical information and data, such as for example DICOM objects, are stored in a (network) file system provided by an operating system. In certain circumstances, doctors and other medical professionals may need to access relevant medical data from multiple file systems pertaining, for example, to data collected as part of a research study. Often, medical data across multiple systems may use different patient identifiers for identification of the same patient. However, to be useful, medical information pertaining to patient data must be modified and integrated into a universal worklist where all of the patient's medical information from various systems is accessible.

The majority of reports produced by diagnostic medical imaging modalities are structured. A structured report is the optimal form of documentation in computerized systems as it allows searching, storage and comparison with similar data elements. Consequently, DICOM structured report increases the efficiency of the distribution of information between various specialties such as computed tomography (CT), magnetic resonance imaging (MRI), ultrasound, etc. In many cases, information contained in structured reports must be read and modified and in certain circumstances, transformation, routing and archiving rules may require accessing data from a DICOM data object and/or from a DICOM structured report.

With the changes in DICOM standards, radiological images and corresponding data may need to be migrated in order to meet current standards. Data migration may be a costly and time-consuming process, often requiring development of a customized software for the migration. This customized solution in turn may present additional challenges. For example, maintaining and upgrading customized software may be cumbersome and costly. As well as ensuring compatibility with industry standard protocols, such as HL7, DICOM, XDS-I, XML and SNMP, QIDO-RS, WADO-RS, STOW-RS, FHIR and/or other protocols which may not always be followed may result in additional support issues.

Therefore, there is a need for a user-configurable radiological data transmission, routing, and archiving engine that provides for integration of patient radiological data into a universal worklist, migration of radiological data to current standards, and user-configurable transformation, routing and archiving of radiological data.

SUMMARY

Compliance with changes in DICOM standards may require radiological images and corresponding data to be upgraded to a new standard as well use of standard protocol (e.g., HL7, DICOM, XDS-I, XML SNMP, DICOMWEB, QIDO-RS, WADO-RS, STOW-RS, FHIR and/or other protocols). The present disclosure is directed towards a user-configurable radiological data transformation, routing, and archiving engine using standard protocols (HL7, DICOM, XDS-I, XML SNMP, DICOMWEB, QIDO-RS, WADO-RS, STOW-RS, FHIR and/or other protocols) to integrate radiological data (patient studies, orders, and reports for example) across disparate radiology systems (e.g., RIS, HIS, EMR, and/or other radiological systems) to provide a universal worklist and/or standardized data. The universal worklist provides a user access to all of a patient's prior studies.

In accordance with one aspect of the invention, the user-configurable radiological data transformation, routing and archiving engine provides for migration of patient radiological data to current standards including DICOM, HL7, and XDS-I, IHE, DICOMWEB, QIDO-RS, WADO-RS, STOW-RS, FHIR and/or other standards.

In accordance with another aspect of the invention, the user-configurable radiological data transformation, routing and archiving engine provides a user with configurable transformation of patient radiological data.

In accordance with another aspect of the invention, the user-configurable radiological data transformation, routing, proxying, integration, and archiving engine provides a user with configurable routing of patient radiological data.

In accordance with another aspect of the invention, the user-configurable radiological data transformation, routing, proxying, integration, and archiving engine provides a user with configurable archiving of patient radiological data.

In accordance with another aspect of the invention, the user-configurable radiological data transformation, routing, proxying, integration, and archiving engine provides a user with configurable pulling of patient radiological data.

In accordance with another aspect of the invention, the user-configurable radiological data transformation, routing, proxying, integration, and archiving engine comprises a software program having computer code processed by a conventional hardware device such as a router or virtual base server.

In accordance with another aspect of the invention, the user-configurable radiological data transformation, routing and archiving engine comprises a plurality of logical sub-engines representing algorithms/routines processed by a conventional device such as a router or virtual base server to provide for user-configurable transformation, routing, proxying, integration, archiving and pulling of patient radiological data.

In accordance with another aspect of the invention, the user-configurable radiological data transformation, routing, proxying, integration, and archiving engine comprises a computer implemented method having steps processed by a computing device such as a router or virtual base server.

In accordance with another aspect of the invention, the user-configurable radiological data transformation, routing, proxying, integration, and archiving engine comprises a computer-implemented method having the steps of providing a graphical user interface (GUD to a user, the GUI providing the user with the ability to configure filter conditions and transformation rules of patient radiological data, receiving the user-configured filter conditions and transformation rules, and processing the user-configured filter conditions and transformation rules in a processor in order to transform patient radiological data.

In accordance with another aspect of the invention, the user-configurable radiological data transformation, routing, proxying, integration, and archiving engine comprises a computer-implemented method having the steps of providing a graphical user interface (GUI) to a user, the GUI providing the user with the ability to configure routing conditions of patient radiological data, receiving the user-configured routing conditions, and processing the user-configured routing conditions in a processor in order to route patient radiological data.

In accordance with another aspect of the invention, the user-configurable radiological data transformation, routing, proxying, integration, and archiving engine comprises a computer-implemented method having the steps of providing a graphical user interface (GUI) to a user, the GUI providing the user with the ability to configure conditions for pulling prior patient radiological data, receiving the user-configured conditions for pulling prior patient radiological data, and processing the user-configured conditions for pulling prior patient radiological data in a processor in order to pull prior patient radiological data.

In accordance with another aspect of the invention, the user-configurable radiological data transformation, routing and archiving engine comprises a computer-implemented method having the steps of providing a GUI to a user, the GUI providing the user with means for configuring events in an DICOM and HL7 workflow, receiving the user-configured events, and processing the user-configured events in a processor in order to transform, route, archive and/or pull patient radiological data.

In accordance with another aspect of the invention, the user-configurable radiological data transformation, routing, proxying, integration, and archiving engine comprises a computer-implemented method having the steps of providing a GUI to a user, the Gill providing the user with means for configuring a data encryption scheme, receiving the user-configured data encryption scheme, and processing the user-configured data encryption scheme in a processor in order to provide a secure connection between devices.

In accordance with another aspect of the invention, the user-configurable radiological data transformation, routing, proxying, integration, and archiving engine comprises a computer-implemented method having the steps of providing a GUI to a user, the GUI providing the user with means for configuring a data compression scheme, receiving the user-configured data compression scheme, and processing the user-configured data compression scheme in a processor in order compress patient radiological data.

In accordance with another aspect of the invention, the user-configurable radiological data transformation, routing, proxying, integration, and archiving engine is communicatively coupled to a network.

There has been outlined, rather broadly, the more important features of the invention in order that the detailed description thereof that follows may be better understood, and in order that the present contribution to the art may be better appreciated. There are, of course, additional features of the invention that will be described below and which will form the subject matter of the claims appended herein.

In this respect, before explaining at least one embodiment of the invention in detail, it is to be understood that the invention is not limited in its application to the details of design and to the arrangement of the components set forth in the following description or illustrated in the drawings. The invention is capable of other embodiments and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other methods and apparatus for carrying out the several purposes of the present invention. It is important, therefore, that the claims be regarded as including such equivalent methods and apparatus insofar as they do not depart from the spirit and scope of the present invention.

BRIEF DESCRIPTION OF THE DRAWINGS

The technology disclosed herein, in accordance with one or more various embodiments, is described in detail with reference to the following figures. The drawings are provided for purposes of illustration only and merely depict typical or example embodiments of the disclosed technology. These drawings are provided to facilitate the reader's understanding of the disclosed technology and shall not be considered limiting of the breadth, scope, or applicability thereof. It should be noted that for clarity and ease of illustration these drawings are not necessarily made to scale.

FIG. 8D is a flowchart of a computer-implemented method of providing a user-configurable data encryption scheme, in accordance with one or more implementations.

FIG. 10 is screenshot of a graphical user interface showing a script editor facility, in accordance with one or more implementations.

FIG. 11 is another screenshot of the graphical user interface showing the script editor facility, in accordance with one or more implementations.

FIG. 21 is screenshot of the graphical user interface of FIG. 20 showing a pop-up box of user-selectable AETitles;

FIG. 24 is a screenshot of the graphical user interface of FIG. 20 showing a pop-up box of user-selectable operands;

FIG. 34 is a screenshot of the graphical user interface of FIG. 32 showing an HL7 message, in accordance with one or more implementations.

FIG. 35 is a screenshot of the graphical user interface of FIG. 32 showing an HL7 message routing, in accordance with one or more implementations.

FIG. 36 is a screenshot of the graphical user interface of FIG. 32 showing a pop-up box of user-selectable tasks, in accordance with one or more implementations.

FIG. 38 is a screenshot of a graphical user interface that provides for user-configurable encryption schemes, in accordance with one or more implementations.

FIG. 39 is a screenshot of the graphical user interface of FIG. 38 showing a pop-up box of user-selectable certificates, in accordance with one or more implementations.

FIG. 42 is a screenshot of a graphical user interface that provides for user-configurable transfer syntaxes, in accordance with one or more implementations.

FIG. 43 is a screenshot of the graphical user interface of FIG. 42 showing additional transfer syntaxes, in accordance with one or more implementations.

FIG. 44 is a screenshot of the graphical user interface of FIG. 42 showing additional transfer syntaxes, in accordance with one or more implementations.

FIG. 45 is a screenshot of the graphical user interface of FIG. 42 showing additional transfer syntaxes, in accordance with one or more implementations.

The figures are not intended to be exhaustive or to limit the invention to the precise form disclosed. It should be understood that the invention can be practiced with modification and alteration, and that the disclosed technology be limited only by the claims and the equivalents thereof.

DETAILED DESCRIPTION OF THE EMBODIMENTS

Figure 1:
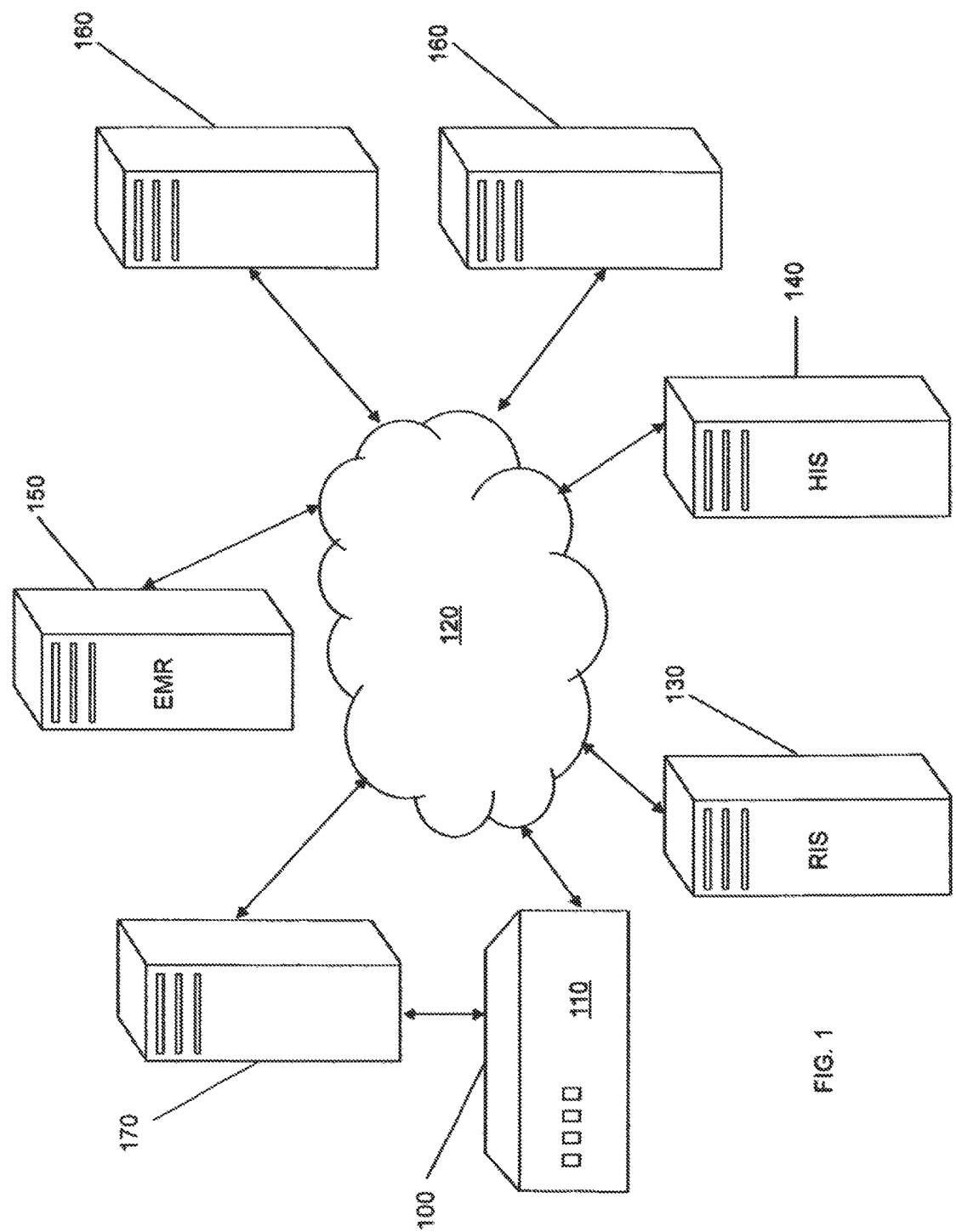
FIG. 1 is a schematic representation of a computing component that may be used in implementing various features of embodiments of the disclosed technology, in accordance with one or more implementations.

The invention will now be described in sufficient detail to enable one skilled in the art to make and use the invention. For purposes of brevity, the user-configurable radiological data transformation, routing and archiving engine will hereinafter be referred to as "the engine" and has been given reference number 100 (FIG. 1).

In its broadest aspect, the engine 100 provides a tool and framework that allows a user to configure the transformation, routing, archiving and storage of patient radiological data. The engine 100 also provides of user-configurable encryption and compression of patient radiological data.

More specifically, the engine 100 comprises a software program and computer-implemented method running on a conventional hardware device 110 such as a router or virtual base server (VMWARE, XEN). The hardware device 110 is communicatively connected to the internet 120 and by this means is communicatively coupled to RIS server 130, HIS server 140, EMR server 150 and other servers 160. In one aspect of the invention, the engine 100 is communicatively coupled directly to a server 170 such as a hospital/clinic/radiologist server.

Figure 2:
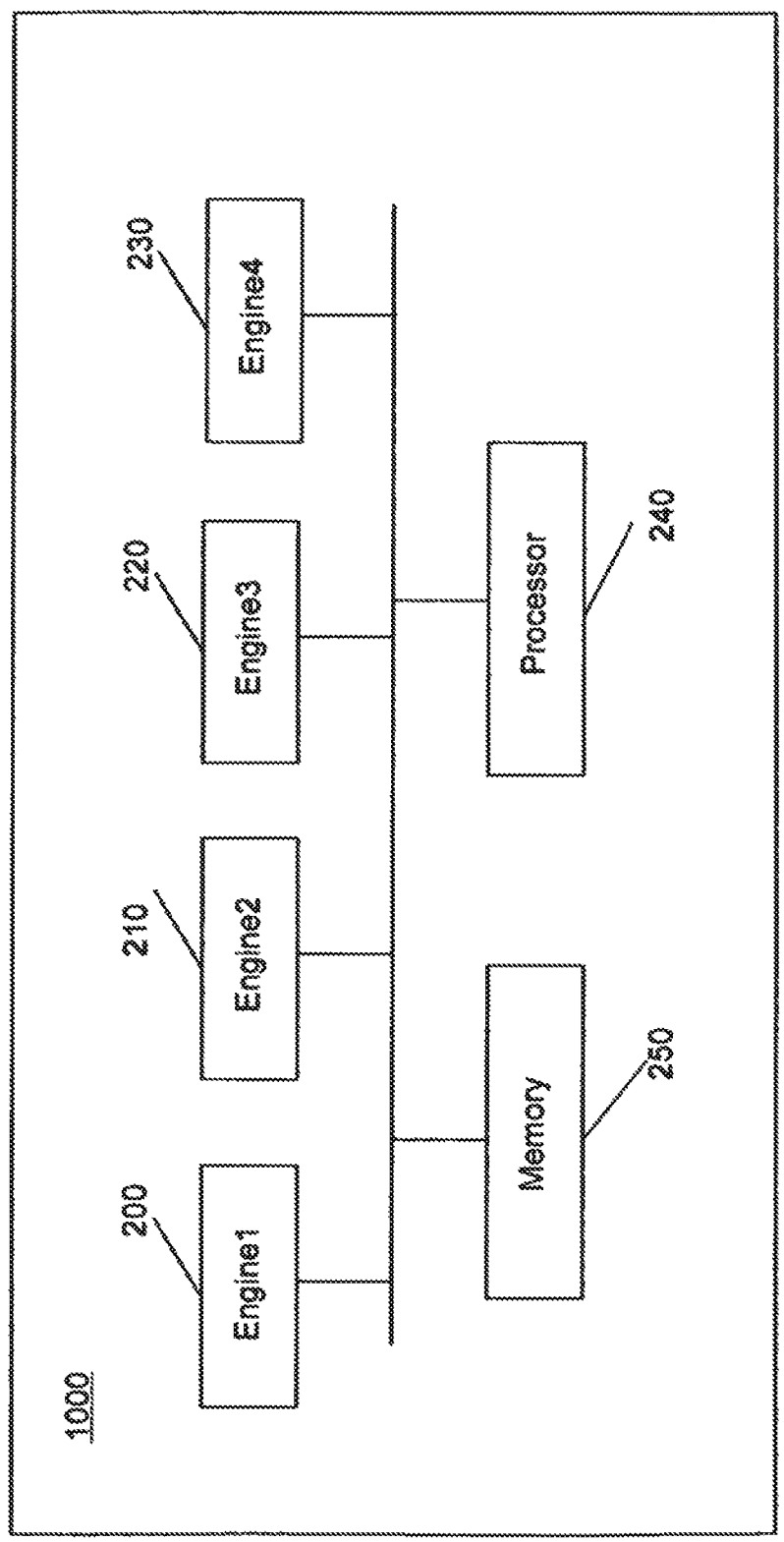
FIG. 2 is a graphical representation of a user-configurable radiological data transformation, routing and archiving engine, in accordance with one or more implementations.

As illustrated in FIG. 2, the engine 100 may be represented by a plurality of sub-engines 200 (engine1), 210 (engine2), 220 (engine3) and 230 (engine4). Sub-engines 200, 210, 220 and 230 are logical representations of algorithms and associated processes/routines stored in a storage medium or memory 250 as computer instructions/code capable of being processed by a processor 240. Other conventional components of the engine 100 such as I/O devices, network interfaces and the like are not shown for simplicity.

Figure 3:
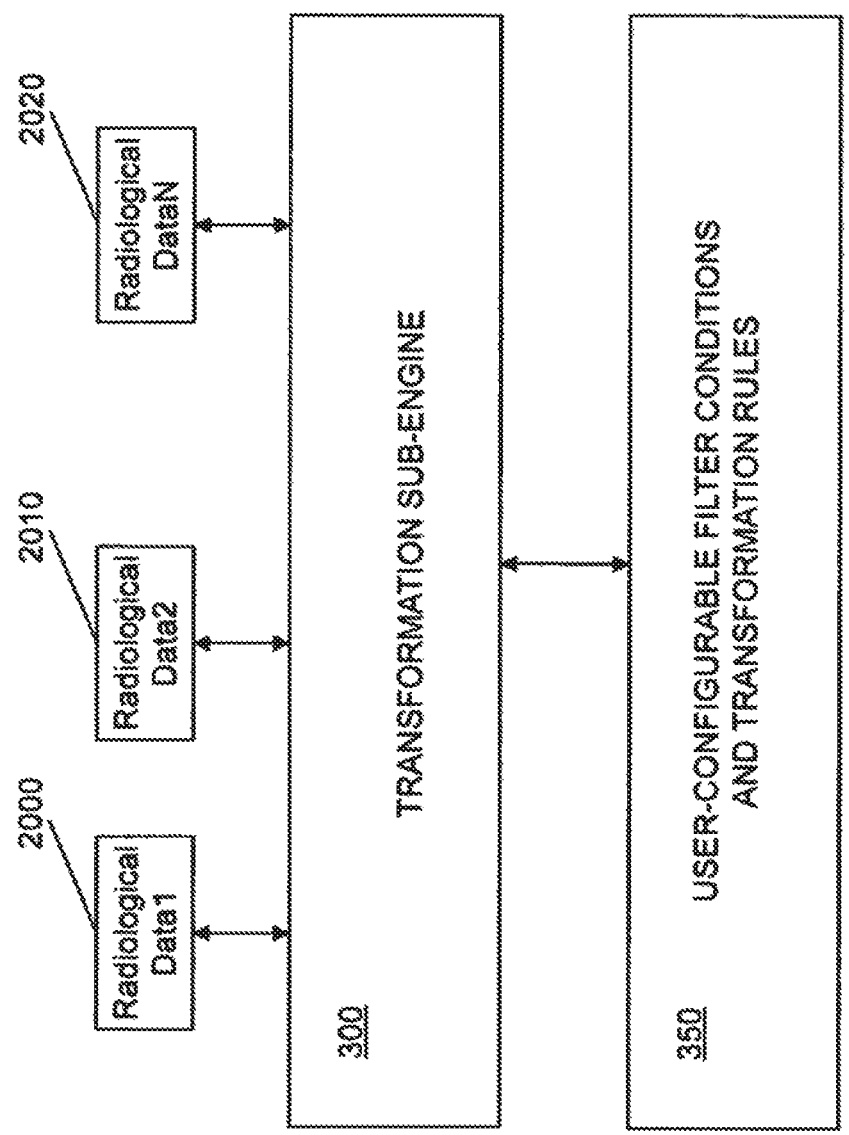
FIG. 3 is a graphical representation of a radiological data transformation sub-engine of the user-configurable radiological data transformation, routing and archiving engine, in accordance with one or more implementations.

A radiological data transformation sub-engine 300 (FIG. 3) uses standard protocols (HL7, DICOM, XML and SNMP) to integrate radiological data 2000 (Radiological Data1), 2010 (Radiological Data2) and 2020 (Radiological DataN) (patient studies, for example) across disparate radiology systems (such as RIS server 130, HIS server 140, and EMR server 150) to provide a universal worklist. The universal worklist provides a user access to all of a patient's prior studies, for example. User-configurable filter conditions and transformation rules 350 provide for transformation of the radiological data 2000, 2010 and 2020 (also referred to as tag morphing) for integration into the universal worklist.

Figure 7:
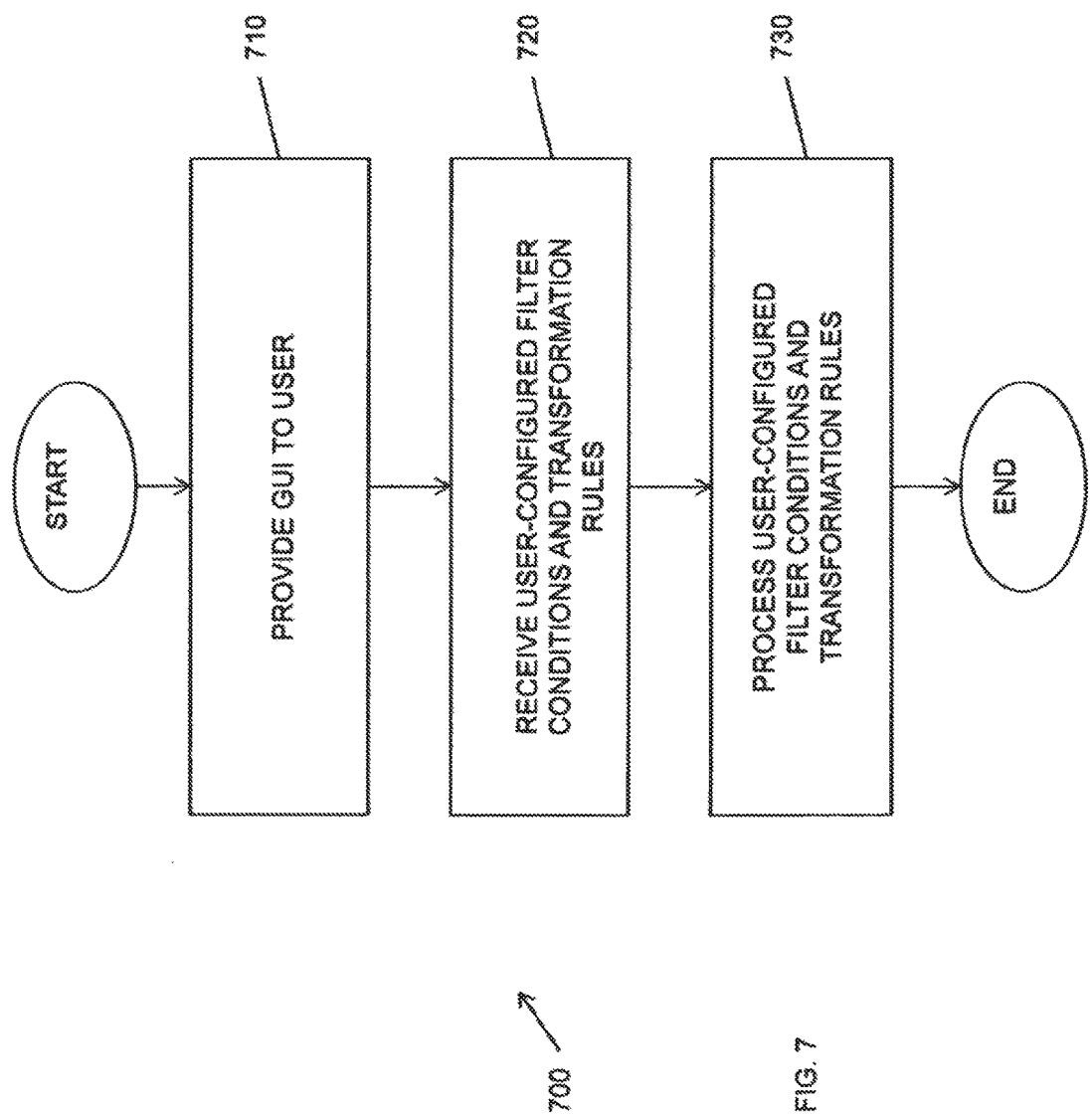
FIG. 7 is a flowchart of a computer-implemented method of providing user-configurable filter conditions and transformation rules, in accordance with one or more implementations.

A computer-implemented method 700 (FIG. 7) in accordance with the invention includes the steps of providing 710 a graphical user to the user, receiving 720 user-configured filter conditions and transformation rules, and processing 730 the user-configured filter conditions and transformations rules in a processor to provide the universal worklist.

Figure 9:
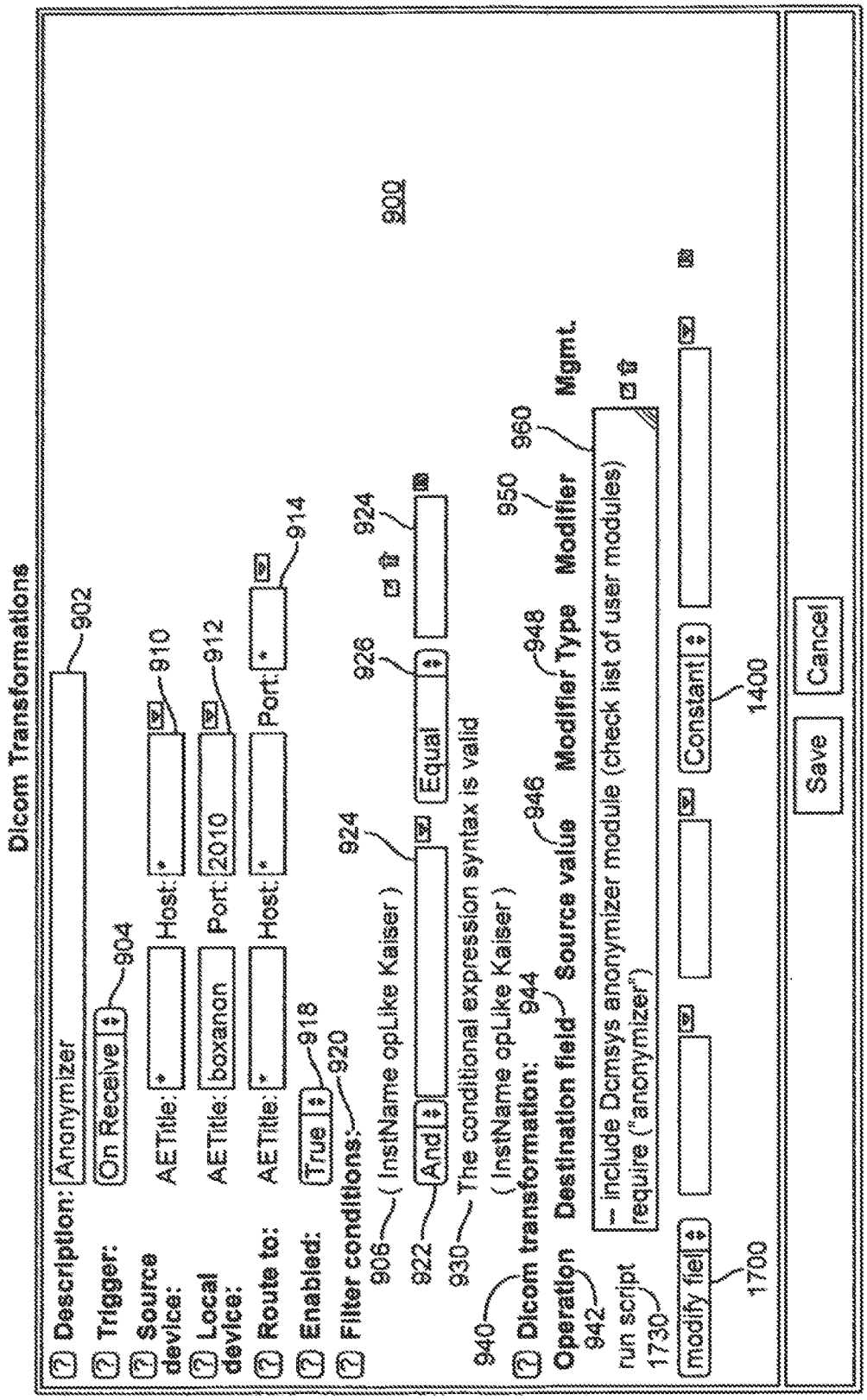
FIG. 9 is a screenshot of a graphical user interface that provides for user-configurable filter conditions and transformation rules, in accordance with one or more implementations.

To provide for user configuration and programming of filter conditions and transformation rules 350, a graphical user interface (GUI) 900 is provided as shown in FIG. 9. The GUI 900 includes a plurality of user-configurable fields including a user-defined Description field 902. A Trigger field 904 is user-configurable to On Receive or On Send. Source device, Local device and Route to fields 910, 912 and 914 respectively are user-configurable to include the application entity title and other information of respective DICOM devices or programs. The DICOM transformation may be enabled (True) or disabled (False) using the Enabled field 918. Filter conditions 920 are user-configurable using the logical operator field 922 (And or Or), the operands fields 924 (comprising DICOM tags 1310 and HL7 Requests 1320 as shown in the pop-up box 1300 of FIG. 13) and the operator field 926. The radiological data transformation sub-engine 300 is operable to provide the user with a confirmation 930 of the syntax of the filter conditions/conditional expression 906.

Figure 14:
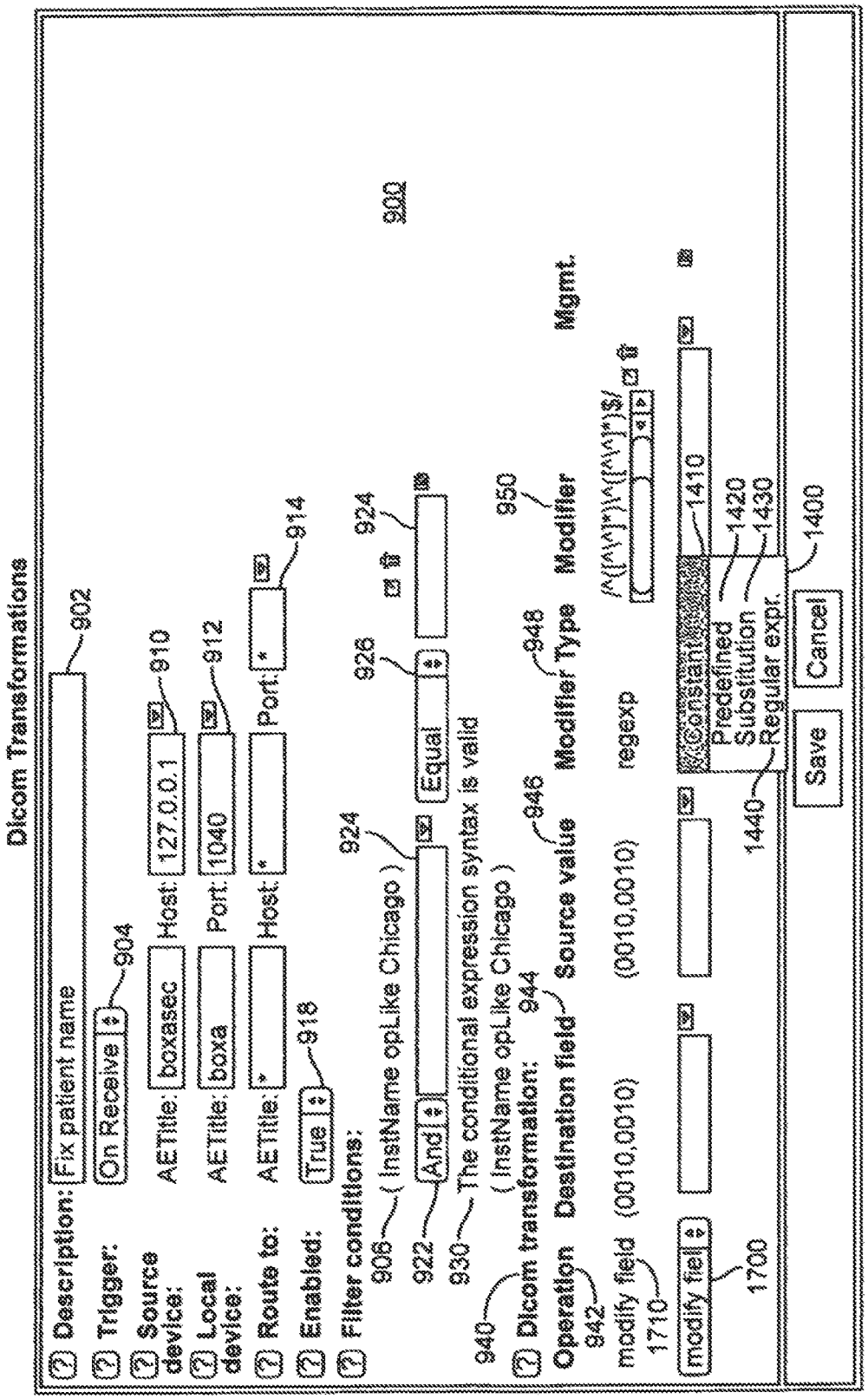
FIG. 14 is a screenshot of the graphical user interface of FIG. 9 showing a pop-up box of user-selectable modifier types, in accordance with one or more implementations.
Figure 17:
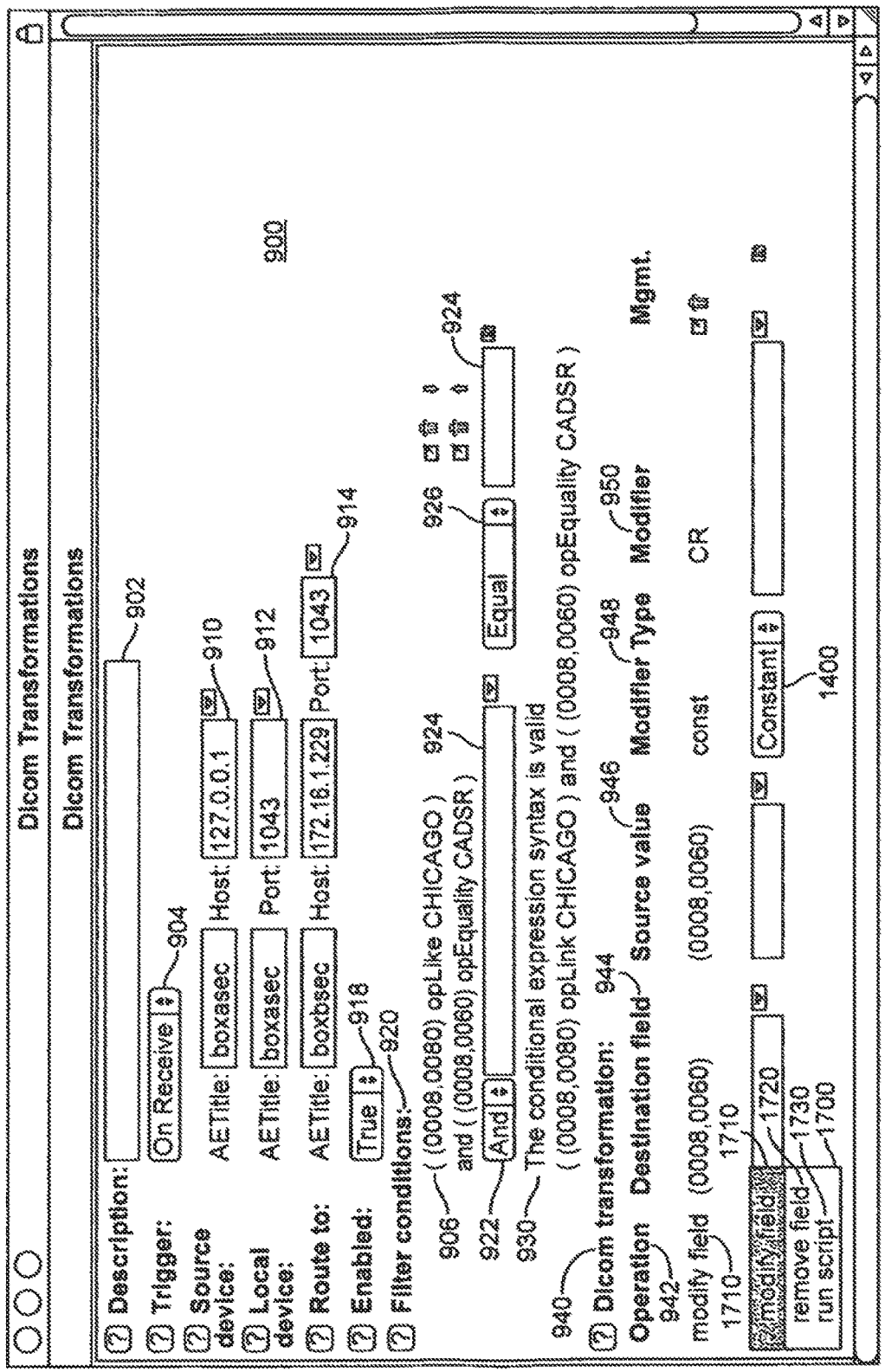
FIG. 17 is a screenshot of the graphical user interface of FIG. 9 that showing a pop-up box of DICOM transformations, in accordance with one or more implementations.

A DICOM transformation field 940 includes the Operation field 942, the Destination field 944, the Source value field 946, the Modifier Type field 948, and the Modifier field 950. The Operation field 942 includes the user-selectable options of modify field 1710, remove field 1720 and run script 1730 as displayed in the pop-up box 1700 in FIG. 17. The Modifier Type field 948 includes the user-selectable options of Constant 1410, Predefined 1420, Substitution 1430 and Regular expr. 1440 as displayed in the pop-up box 1400 in FIG. 14.

Figure 11:
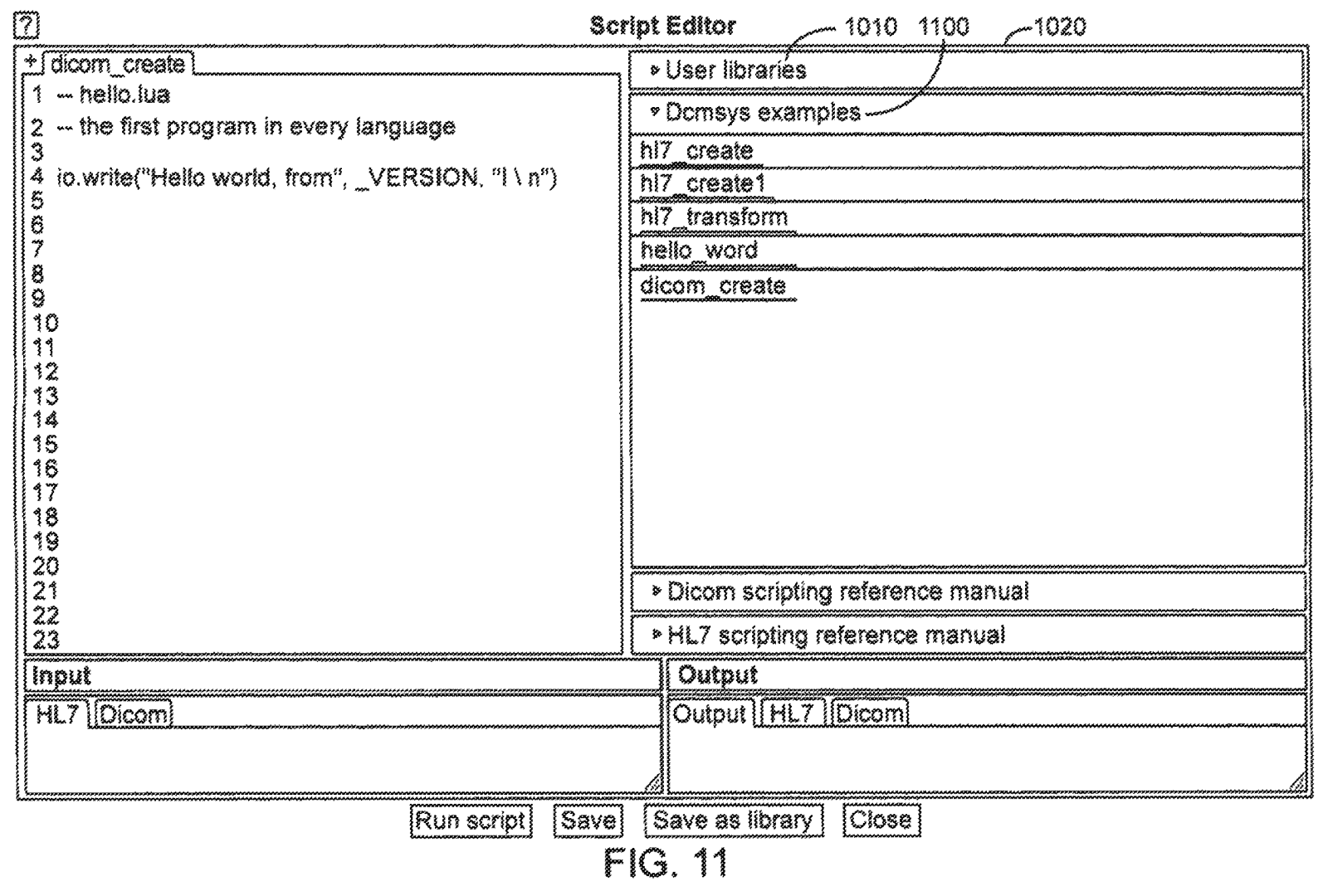

In the GUI 900 of FIG. 9, the run script operation 1730 is selected and comprises the "anonymizer" script 1000 shown in FIG. 10. The "anonymizer" script 1000 is shown as part of a User Library 1010 of a Script Editor GUI 1020. The script editor enables a user to write script in a scripting language such as LUA to provide for user-programmable transformations of the radiological data. Also available to the user are vendor-provided scripts 1030 as shown in FIG. 11.

Figure 12:
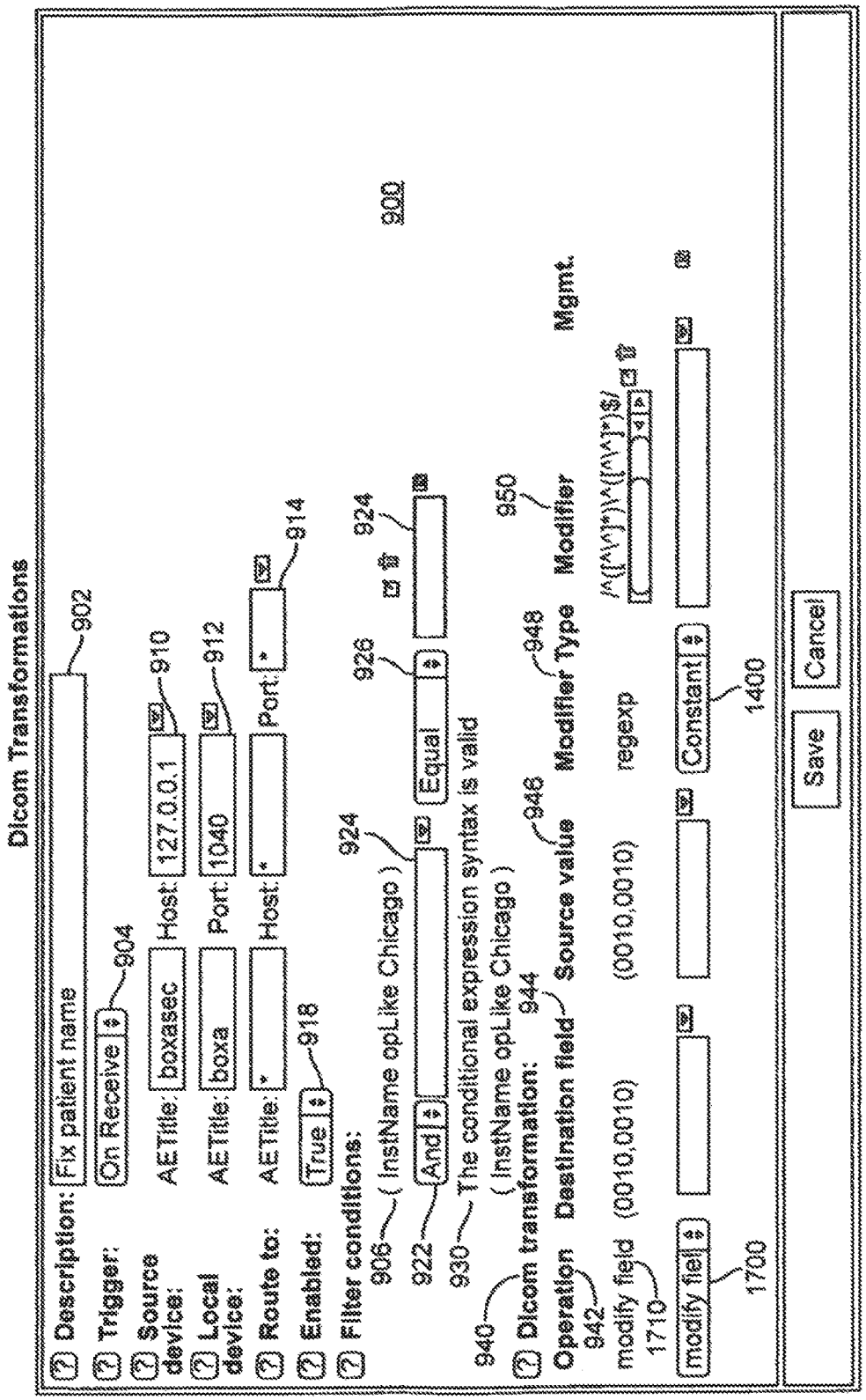
FIG. 12 is another screenshot of the graphical user interface of FIG. 9, in accordance with one or more implementations.

With reference to FIG. 12, the DICOM transformation is entitled "Fix patient name" and the operation modify field 1710 is selected. Values of the Destination field 944 and Source value 946 are shown. In addition the Modifier Type is shown as regexp.

Figure 13:
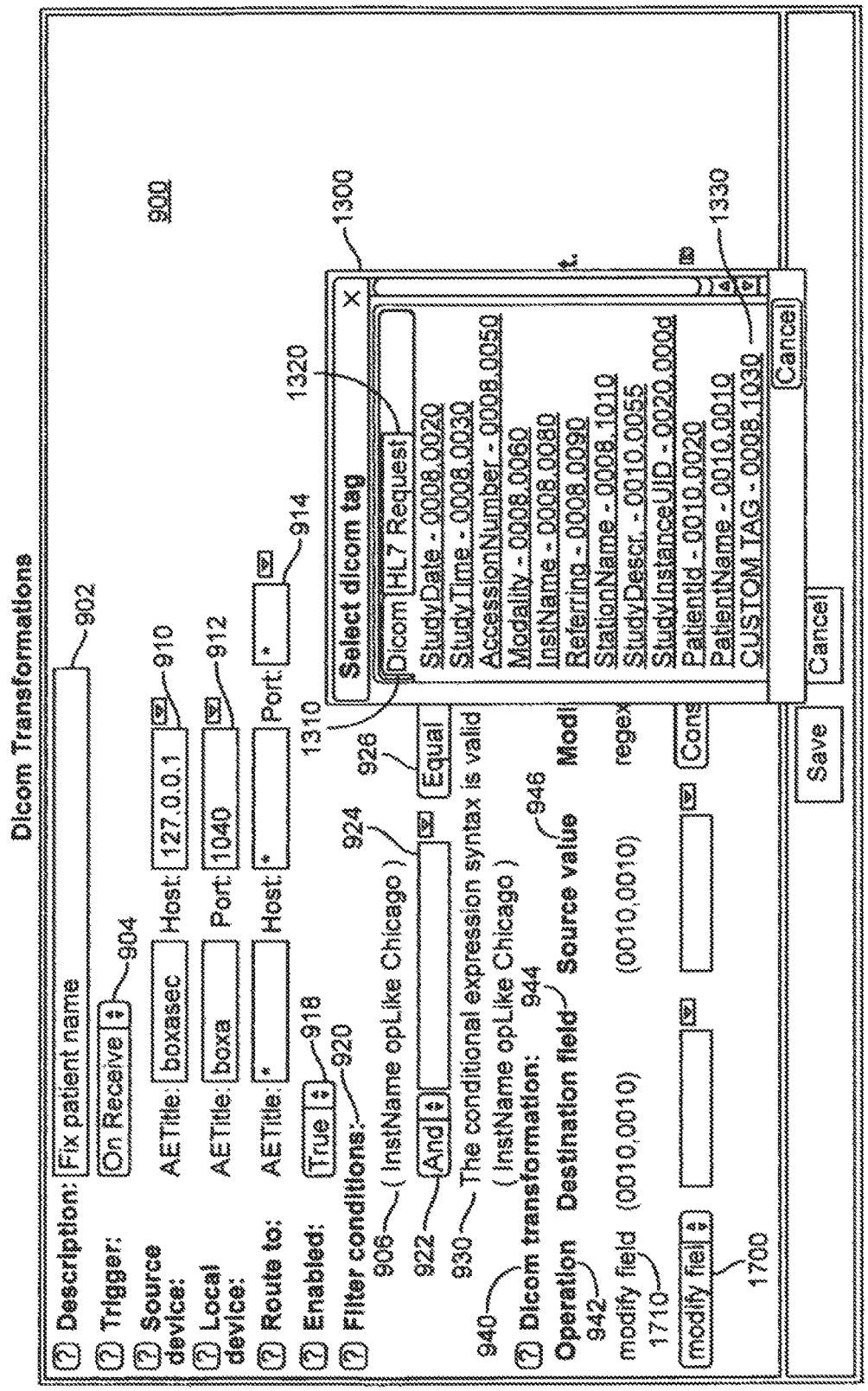
FIG. 13 is a screenshot of the graphical user interface of FIG. 9 showing a pop-up box of user-selectable DICOM tag, in accordance with one or more implementations.

As previously noted, the operands fields 924 are user-selectable from the DICOM tags 1310 displayed in the pop-up box 1300 (FIG. 13). In addition to standard DICOM tags such as StudyDate, StudyTime, AccessionNmber, Modality, InstName, Referring, StationName, StudyDescr, StudyInstanceUID, PatientID, and PatientName, custom tags (such as CUSTOM TAG 1330) are user-configurable. By way of example, a custom tag could include a measurement such as density of a bone or a particular word or words in the radiological data.

Figure 18:
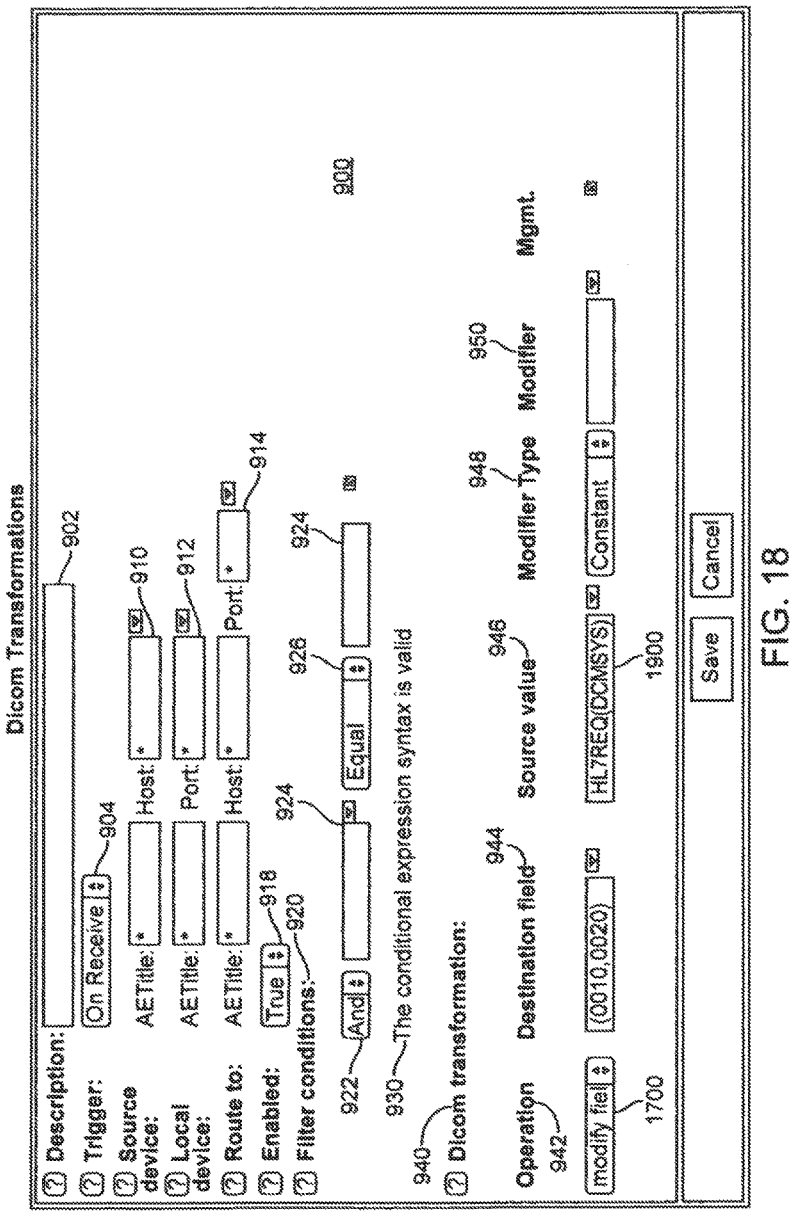
FIG. 18 is a screenshot of the graphical user interface of FIG. 9 showing a user-configurable source value, in accordance with one or more implementations.
Figure 19:
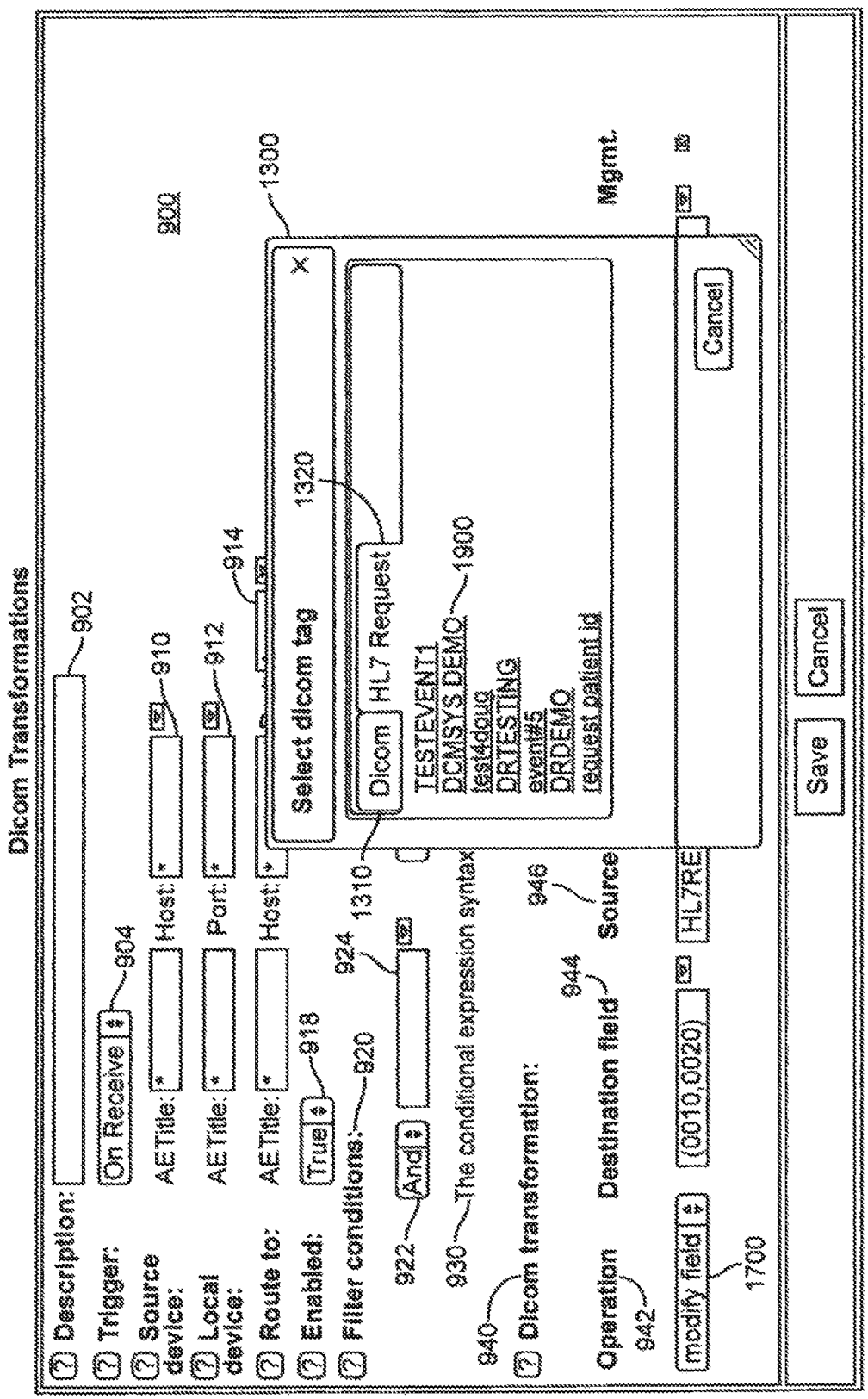
FIG. 19 is a screenshot of the graphical user interface of FIG. 9 showing a pop-up box of user-selectable source values, in accordance with one or more implementations.

The pop-up box 1300 also includes user-configurable HL7 Request 1320 options as shown in FIG. 19. As shown in FIG. 18, the source value 946 is selected to be the HL7 Request DCMSYS DEMO 1900.

Figure 15:
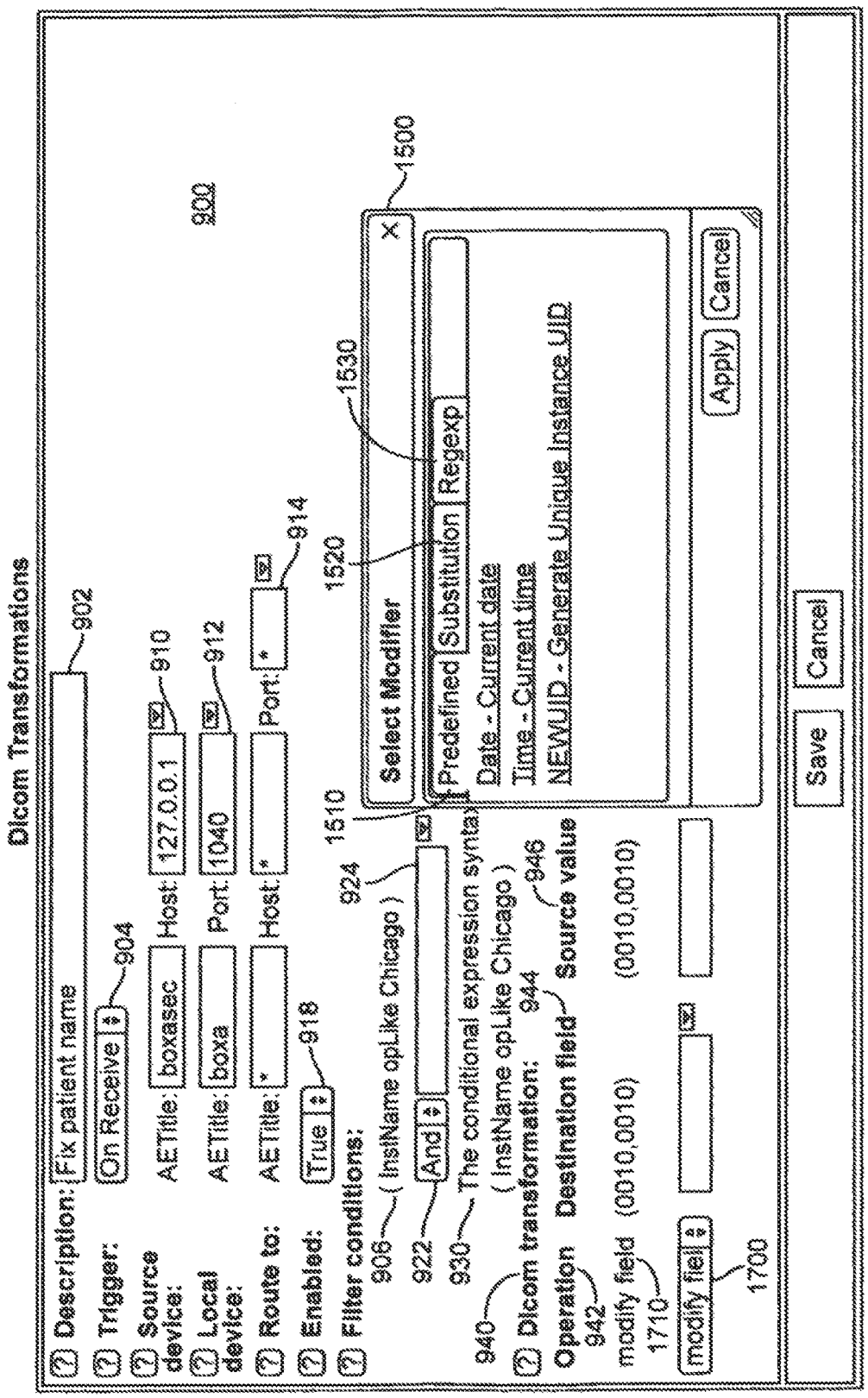
FIG. 15 is a screenshot of the graphical user interface of FIG. 9 showing a pop-up box of user-selectable pre-defined modifiers, in accordance with one or more implementations.
Figure 16:
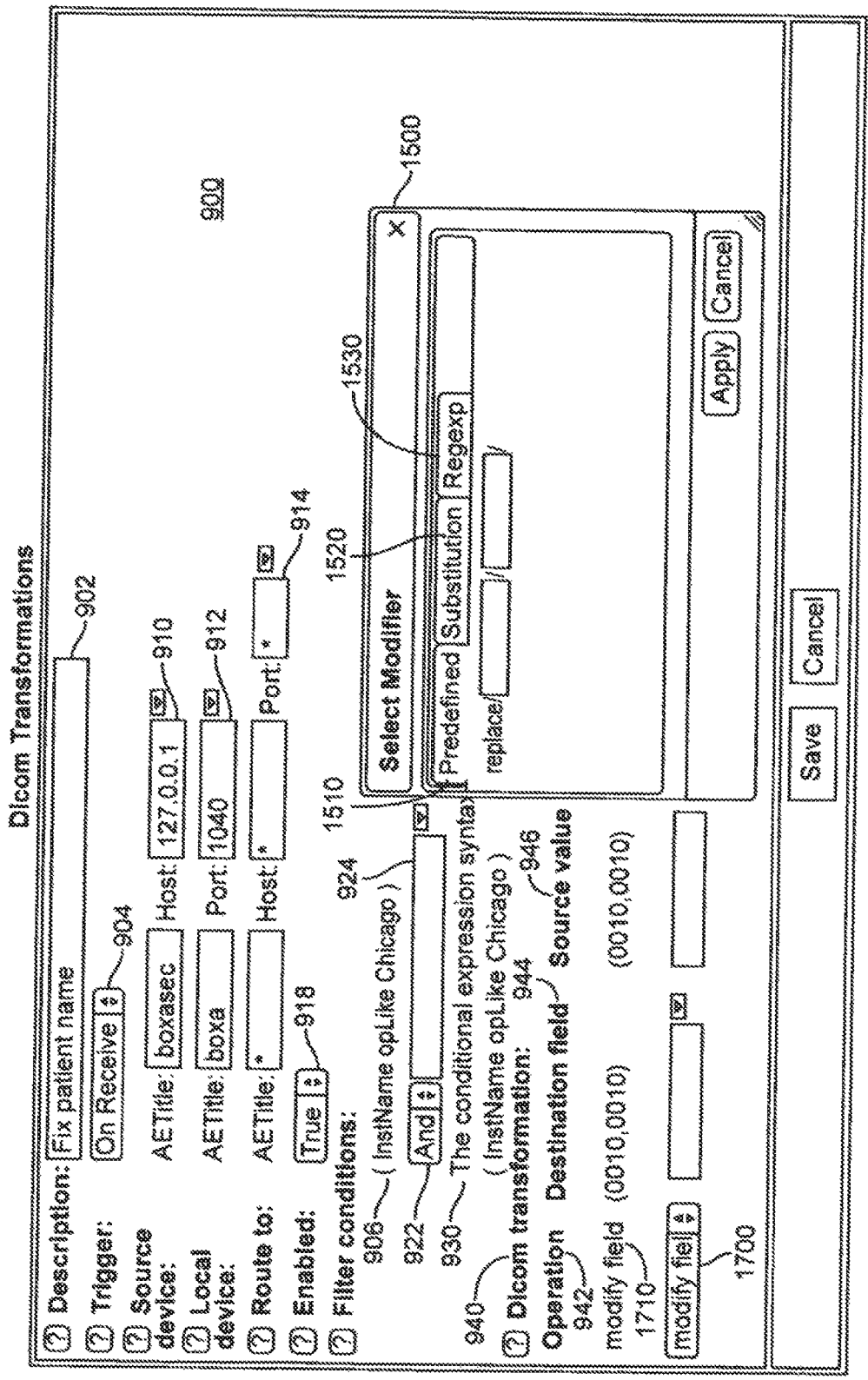
FIG. 16 is a screenshot of the graphical user interface of FIG. 9 showing a pop-up box of user-selectable Regexp modifiers, in accordance with one or more implementations.

Finally, with reference to FIG. 15 and FIG. 16, a Select Modifier pop-up box 1500 includes Predefined modifiers 1510, Substitution modifiers 1520 and Regexp modifiers 1530.

Figure 4:
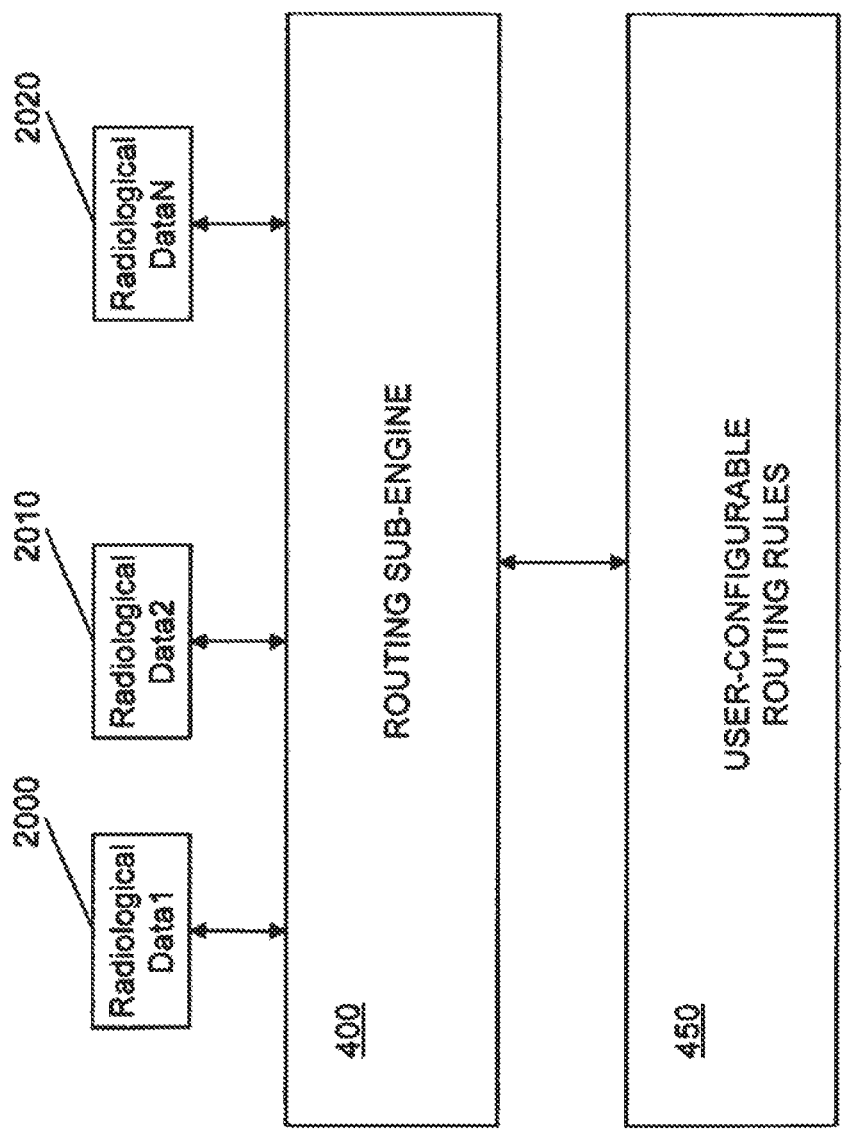
FIG. 4 is a graphical representation of a radiological data routing sub-engine of the user-configurable radiological data transformation, routing and archiving engine, in accordance with one or more implementations.

A radiological data routing sub-engine 400 (FIG. 4) uses standard protocols (HL7, DICOM, XML and SNMP) to route radiological data 2000 (Radiological Data1), 2010 (Radiological Data2) and 2020 (Radiological DataN) (patient studies, for example) from disparate radiology systems (such as RIS server 130, HIS server 140, and EMR server 150) to provide for migration to a common standard. User-configurable routing rules 450 provide for routing of the radiological data 2000, 2010 and 2020.

Figure 8:
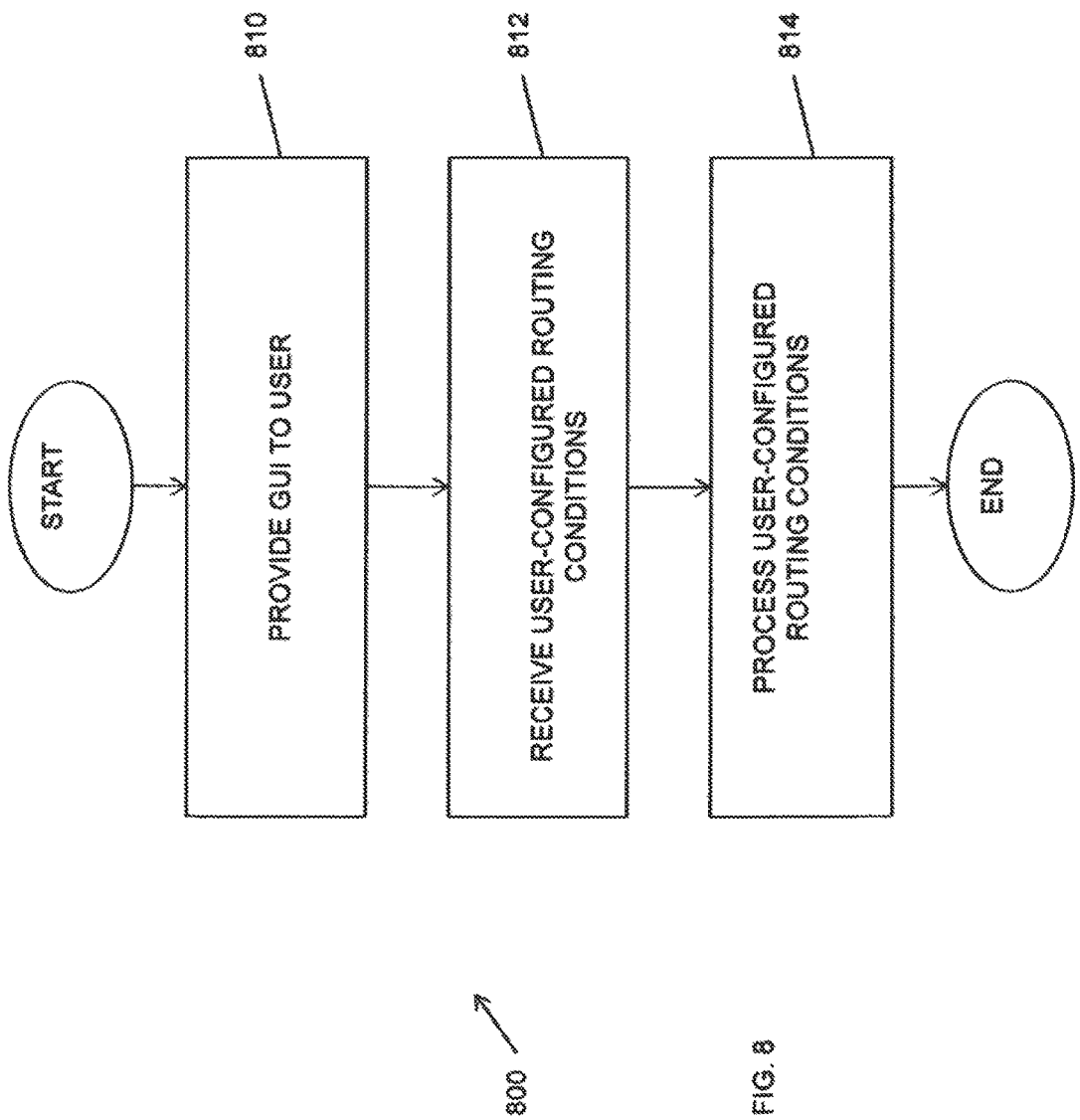
FIG. 8 is a flowchart of a computer-implemented method of providing user-configurable routing conditions, in accordance with one or more implementations.

A computer-implemented method 800 (FIG. 8) in accordance with the invention includes the steps of providing 810 a graphical user to the user, receiving 812 user-configured routing conditions, and processing 814 the user-configured routing conditions in a processor to provide for standardized routing of patient radiological data.

Figure 20:
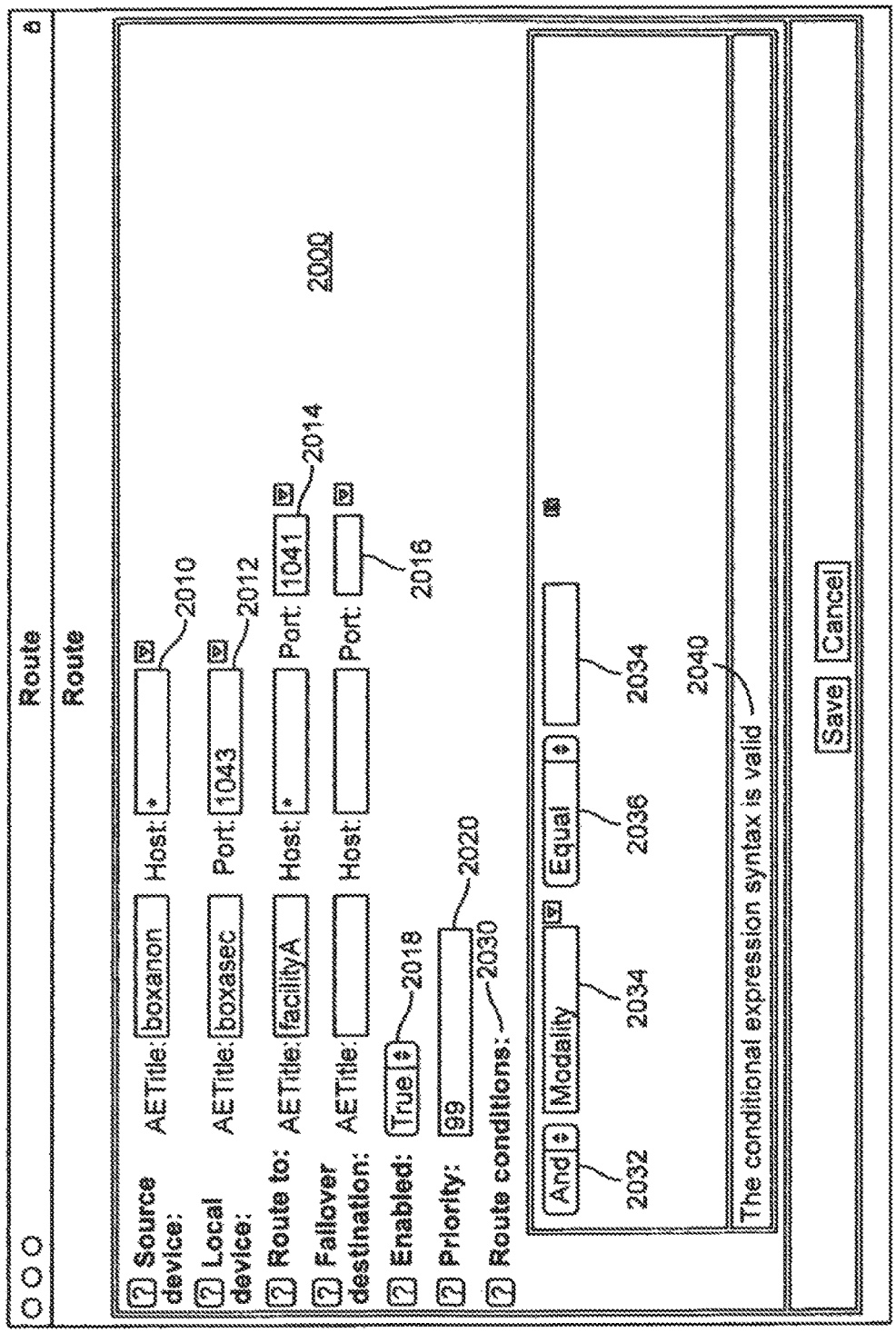
FIG. 20 is a screenshot of a graphical user interface that provides for user-configurable radiological data routing, in accordance with one or more implementations.

To provide for user configuration and programming of routing conditions 450, a graphical user interface (GUI) 2000 is provided as shown in FIG. 20. The GUI 2000 includes a plurality of user-configurable fields including Source device, Local device, Route to, and Failover destination fields 2010, 2012, 2014 and 2016 respectively. Fields 2010, 2012, 2014 and 2016 are user-configurable to include the application entity title and other information of respective DICOM devices or programs. Routing may be enabled (True) or disabled (False) using the Enabled field 2018. A Priority field 2020 provides for user-configurable prioritization of the routing.

A Route conditions field 2030 provides for user-configurable routing conditions including a logical operator field 2032, operands fields 2034, and the operator field 2036. The radiological data routing sub-engine 400 is operable to provide the user with a confirmation 2040 of the syntax of the routing conditions 2030.

Figure 22:
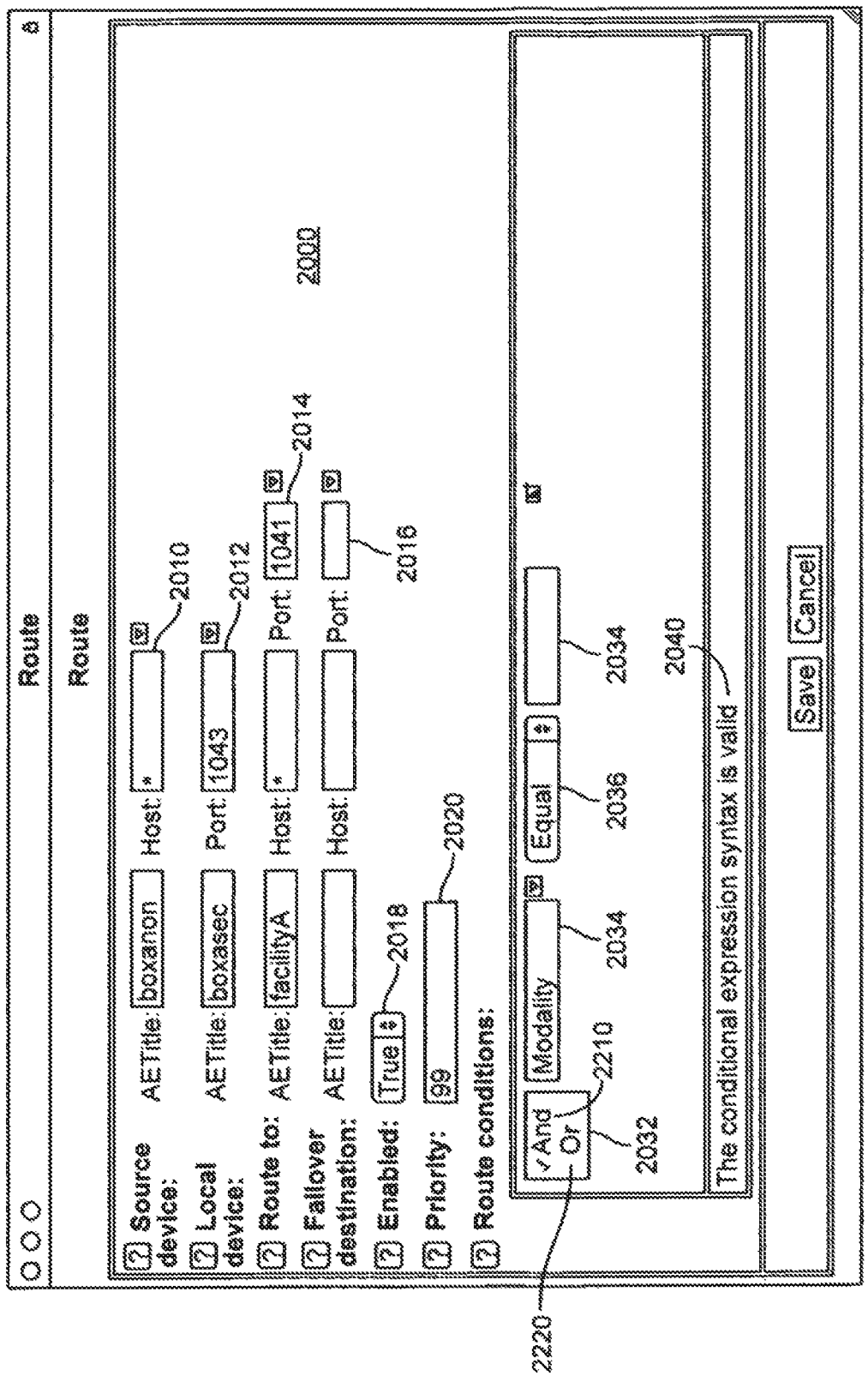
FIG. 22 is a screenshot of the graphical user interface of FIG. 20 showing a pop-up box of user-selectable logical operators.
Figure 23:
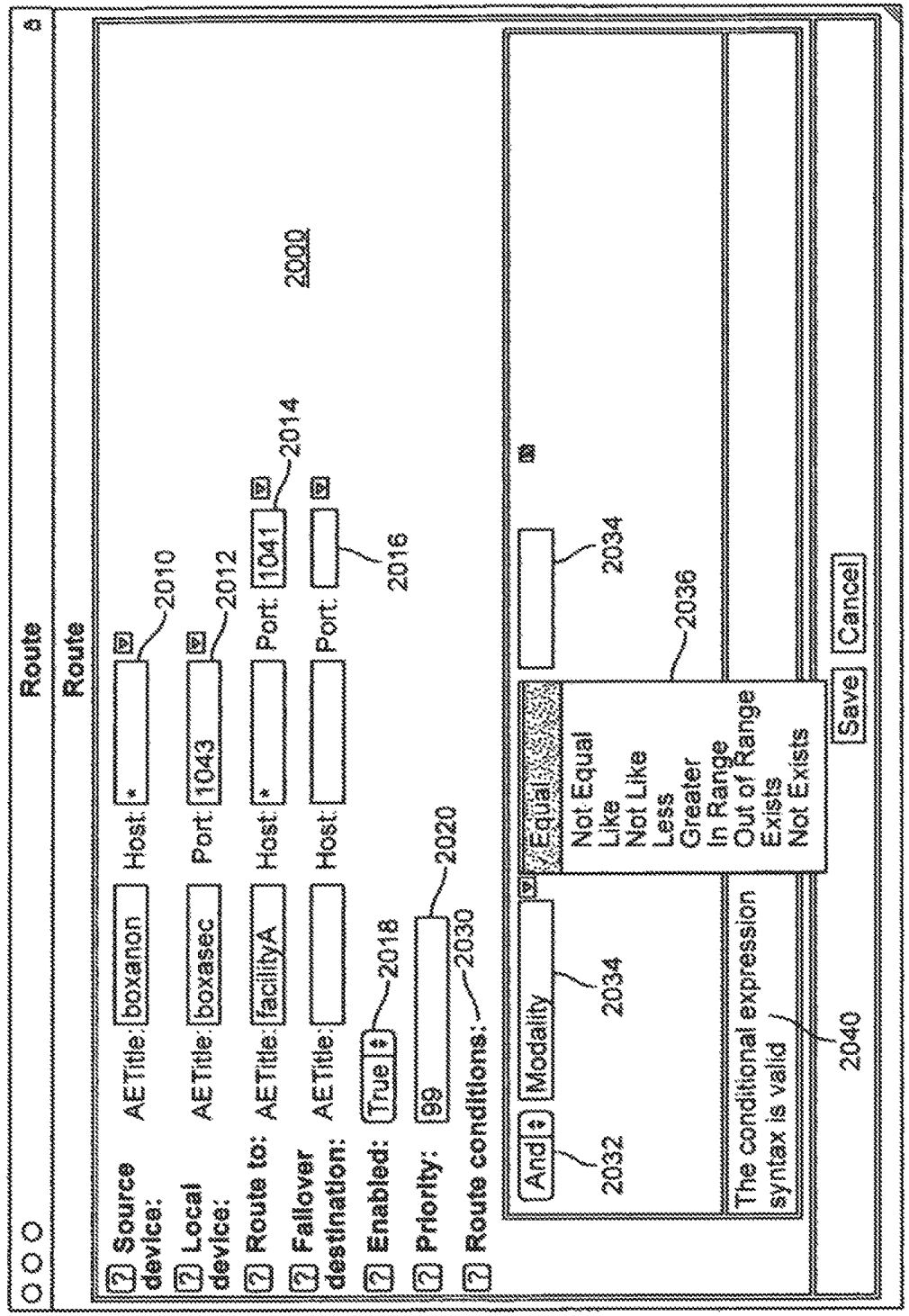
FIG. 23 is a screenshot of the graphical user interface of FIG. 20 showing a pop-up box of user-selectable logical conditions.
Figure 24:
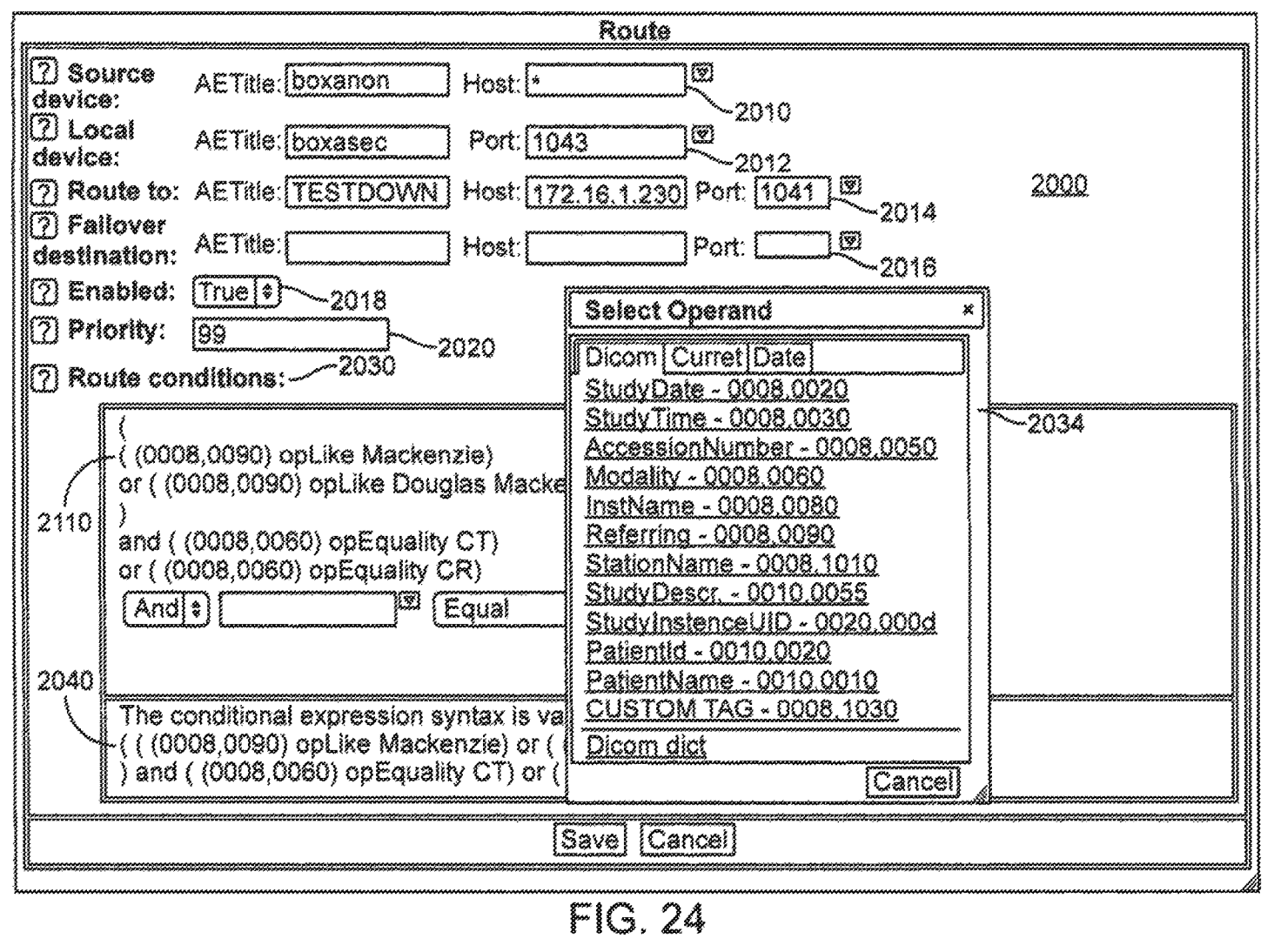

With reference to FIG. 21, a pop-up box 2100 is shown from which the user may select the application entity titles of the fields 2010, 2012, 2014 and 2016. FIG. 22 illustrates the logical operator field that includes the logical operators And 2210 and Or 2220. FIG. 23 illustrates the operator field 2036 that includes Equal, Not Equal, Like, Not Like, Less, Greater, In Range, Out of Range, Exists, and Not Exists. FIG. 24 illustrates the user-selectable operands field 2034 that includes DICOM tags StudyDate, StudyTime, AccessionNumber, Modality, InstName, Referring, StationName, StudyDescr, StudyinstanceUID, PatientID, PatientName, and the user-configurable CUSTOM TAG. FIG. 24 also shows an exemplary routing condition 2110 (also shown in FIG. 21).

Figure 5:
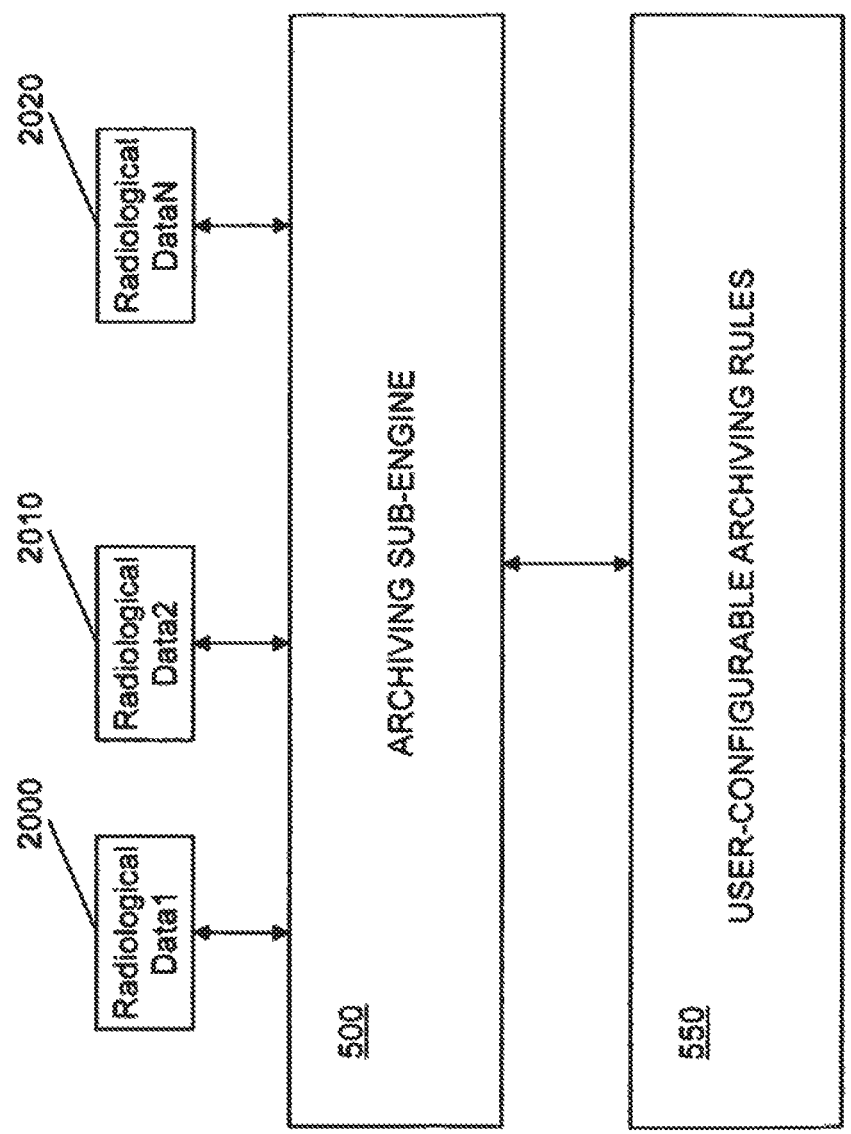
FIG. 5 is a graphical representation of a radiological data archiving sub-engine of the user-configurable radiological data transformation, routing and archiving engine, in accordance with one or more implementations.

A radiological data archiving sub-engine 500 (FIG. 5) uses standard protocols (HL7, DICOM, XML and SNMP) to archive radiological data 2000 (Radiological Data1), 2010 (Radiological Data2) and 2020 (Radiological DataN) (patient studies, for example) from disparate radiology systems (such as RIS server 130, HIS server 140, and EMR server 150). User-configurable rules 550 provide for archiving of the radiological data 2000, 2010 and 2020.

Figure 8A:
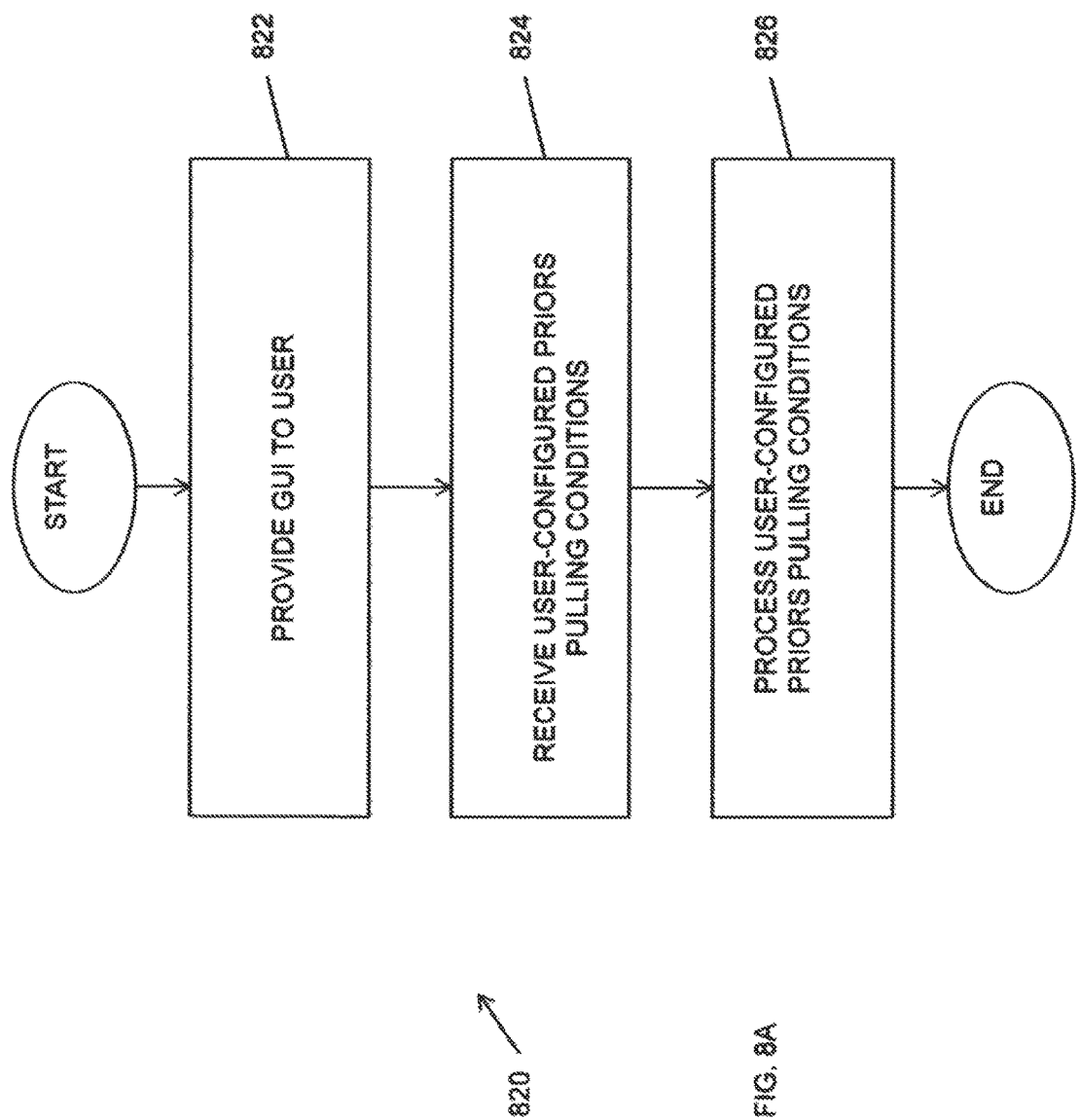
FIG. 8A is a flowchart of a computer-implemented method of providing user-configurable priors pulling conditions, in accordance with one or more implementations.
Figure 8B:
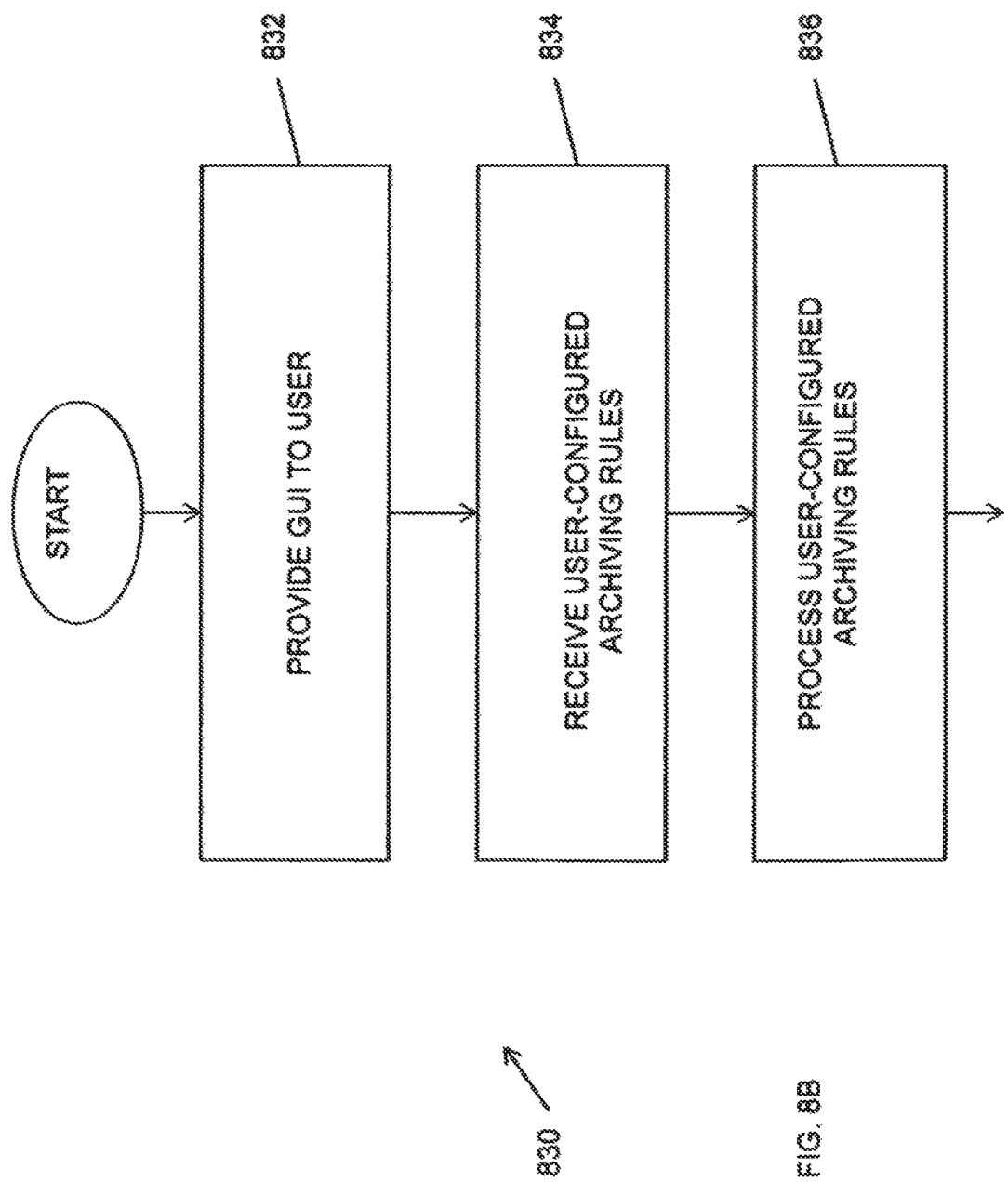
FIG. 8B is a flowchart of a computer-implemented method of providing archiving rules, in accordance with one or more implementations.

A computer-implemented method 830 (FIG. 8B) in accordance with the invention includes the steps of providing 832 a graphical user to the user, receiving 834 user-configured archiving rules, and processing 836 the user-configured archiving rules in a processor to provide for archiving of patient radiological data.

Figure 25:
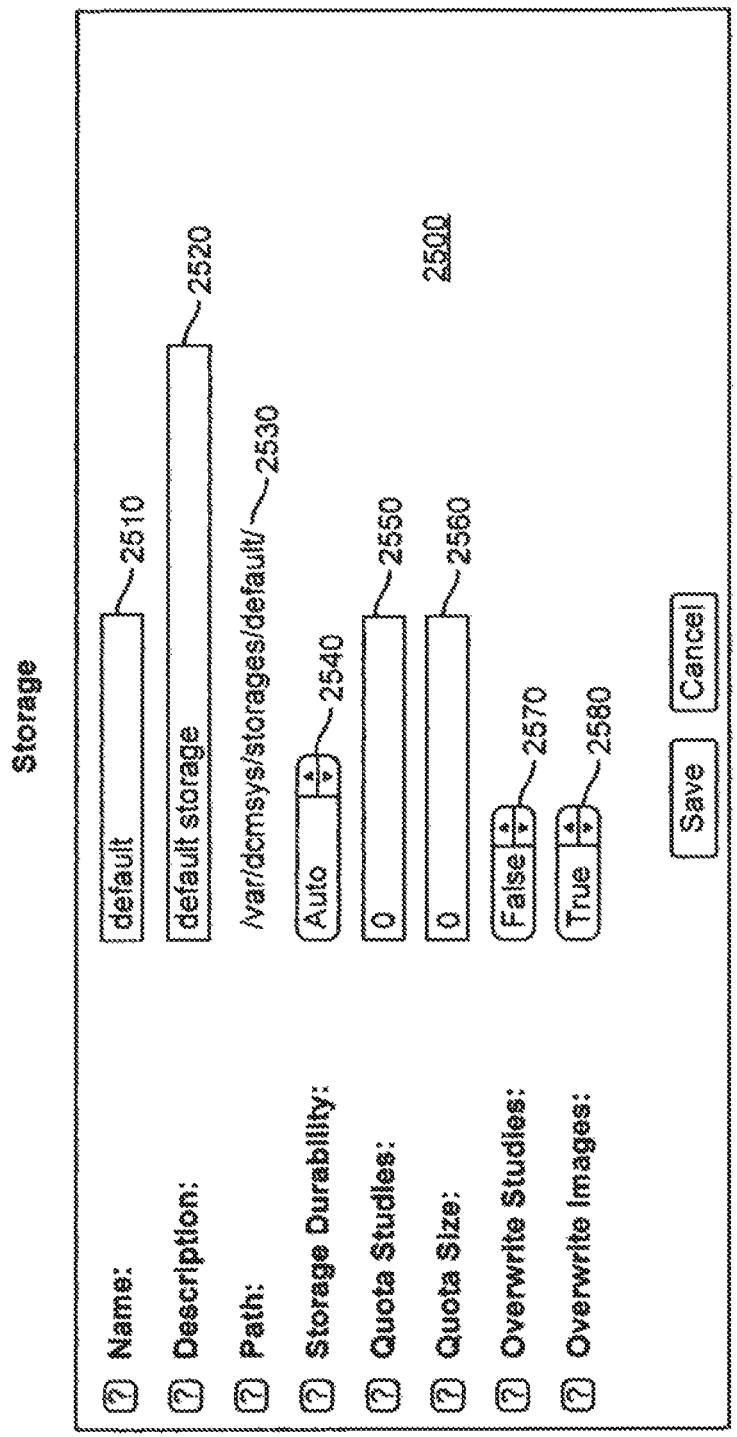
FIG. 25 is screenshot of a graphical user interface that provides for user-configurable radiological data archiving.
Figure 26:
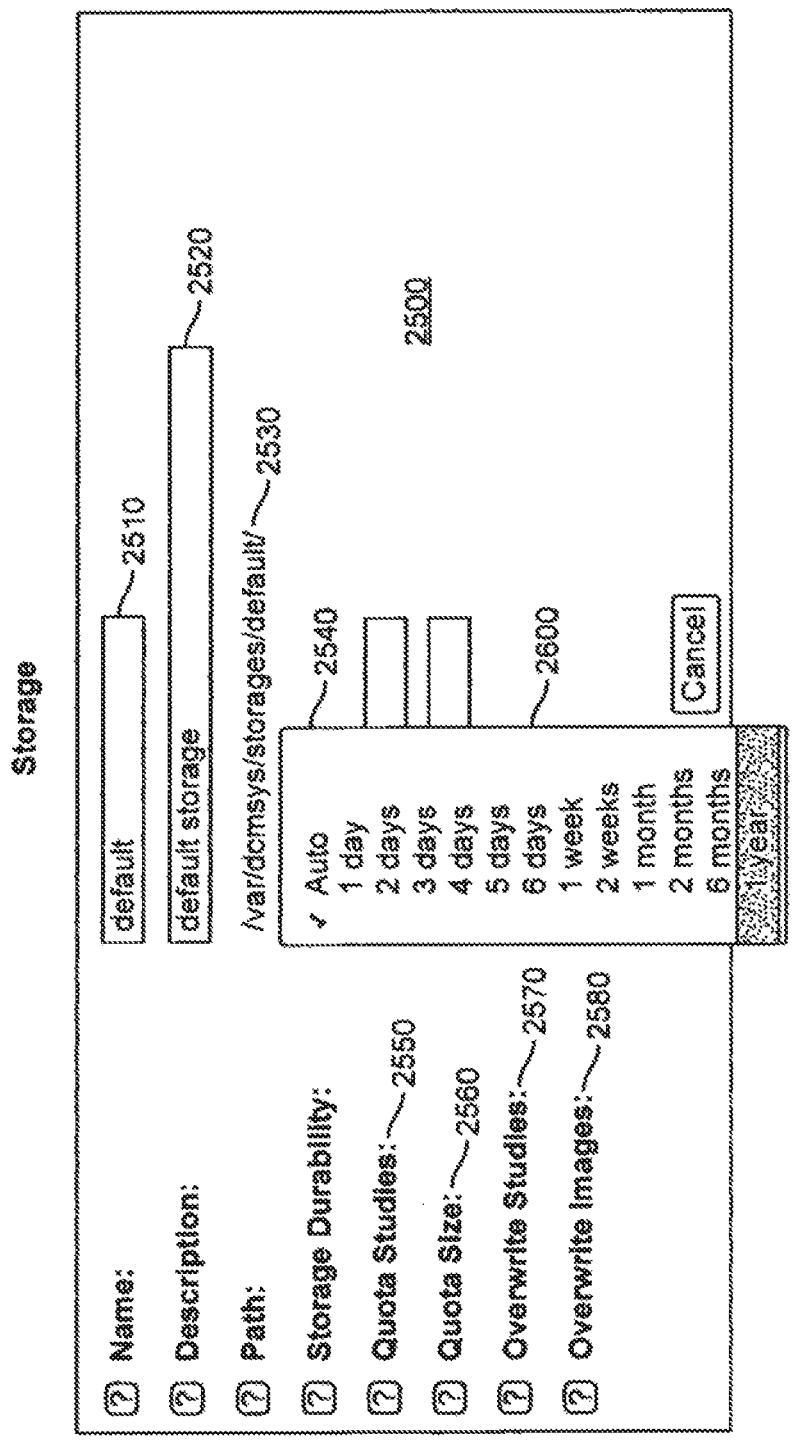
FIG. 26 is a screenshot of the graphical user interface of FIG. 30 showing a pop-up box of user-selectable storage duration.

To provide for user configuration and programming of archiving rules 550, a graphical user interface (GUI) 2500 is provided as shown in FIG. 25. The GUI 2500 includes a plurality of user-configurable fields including Name 2510, Description 2520, Path 2530, Storage Durability 2540, Quota Studies 2550, Quota Size 2560, Overwrite Studies 2570 and Overwrite Images 2580. Storage Durability 2540 provides a pop-up window 2600 (FIG. 26) providing user-selected storage duration. Overwrite Studies 2570 and Overwrite Images 2580 may be selected as either True or False.

Figure 6:
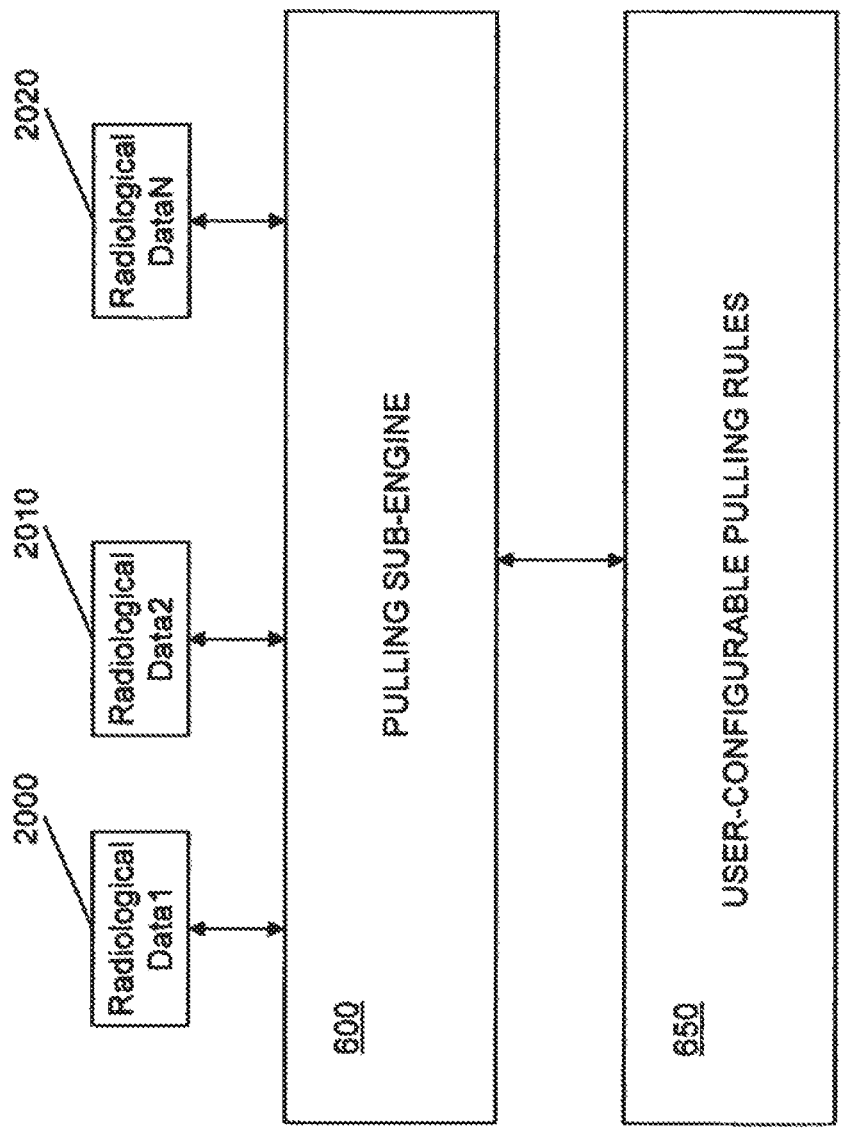
FIG. 6 is a graphical representation of a radiological data pulling sub-engine of the user-configurable radiological data transformation, routing and archiving engine, in accordance with one or more implementations.

A radiological data priors puller sub-engine 600 (FIG. 6) uses standard protocols (HL7, DICOM, XML and SNMP) to pull prior radiological data 2000 (Radiological Data1), 2010 (Radiological Data2) and 2020 (Radiological DataN) (patient studies, for example) from disparate radiology systems (such as RIS server 130, HIS server 140, and EMR server 150). User-configurable puller rules 650 provide for pulling prior radiological data 2000, 2010 and 2020.

A computer-implemented method 820 (FIG. 8A) in accordance with the invention includes the steps of providing 822 a graphical user to the user, receiving 824 user-configured pulling conditions, and processing 826 the user-configured pulling conditions a processor to provide for pulling of prior patient radiological data.

Figure 27:
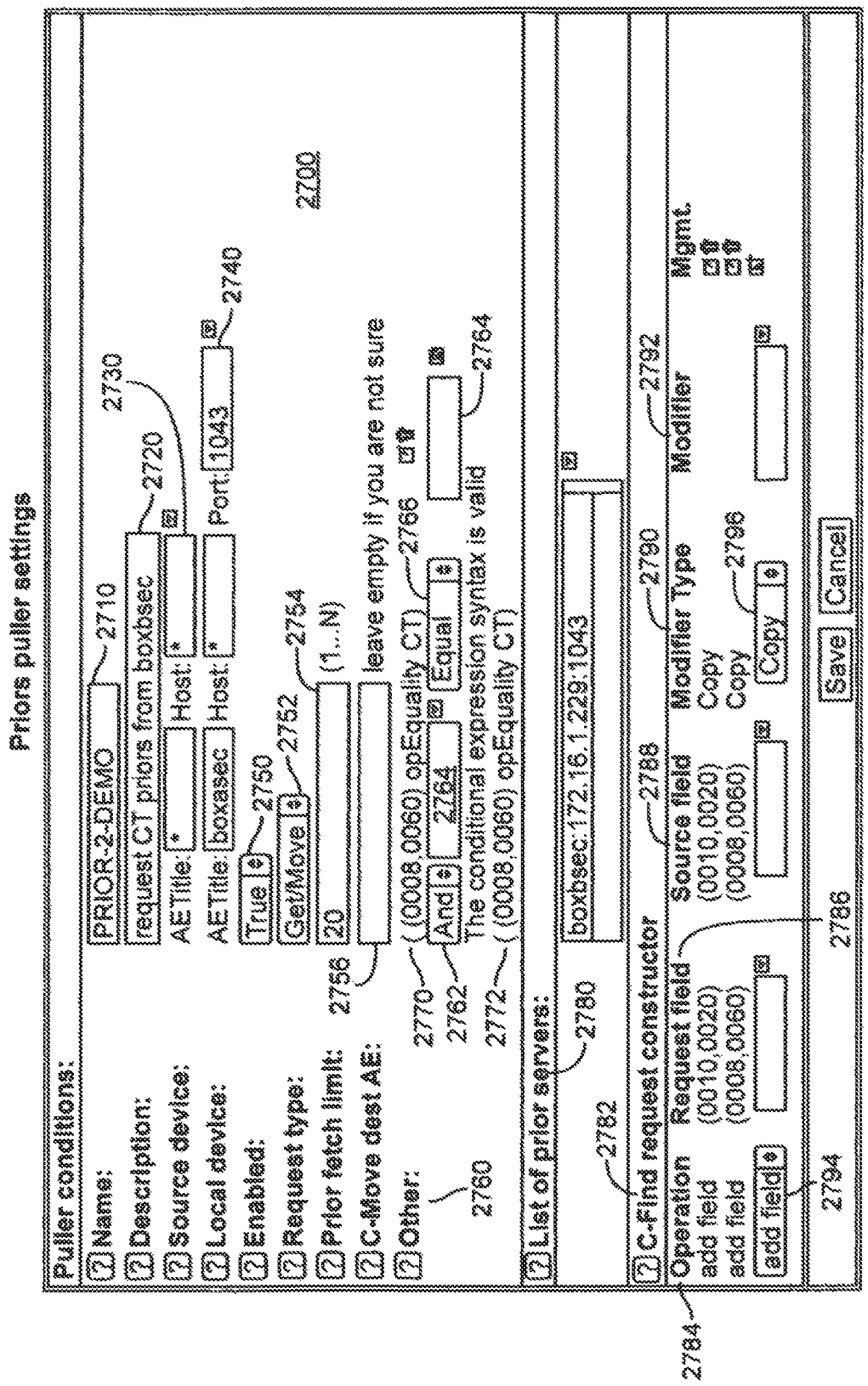
FIG. 27 is a screenshot of a graphical user interface that provides for user-configurable radiological data pulling.

To provide for user configuration and programming of priors puller rules 650, a graphical user interface (GUI) 2700 is provided as shown in FIG. 27. The GUI 2700 includes a plurality of user-configurable fields including Name 2710 and Description 2720. Source device and Local device fields 2730 and 2740 respectively are user-configurable to include the application entity title and other information of respective DICOM devices or programs. Pulling priors may be enabled (True) or disabled (False) using the Enabled field 2750. The type of request is user-configurable using the Request type field 2752 and includes Get and Move functions. A Prior fetch limit field provides the user with a means of selecting the limit of priors fetched.

The destination of the C-Move request is selectable using the C-Move dent AE field 2756.

Figure 29:
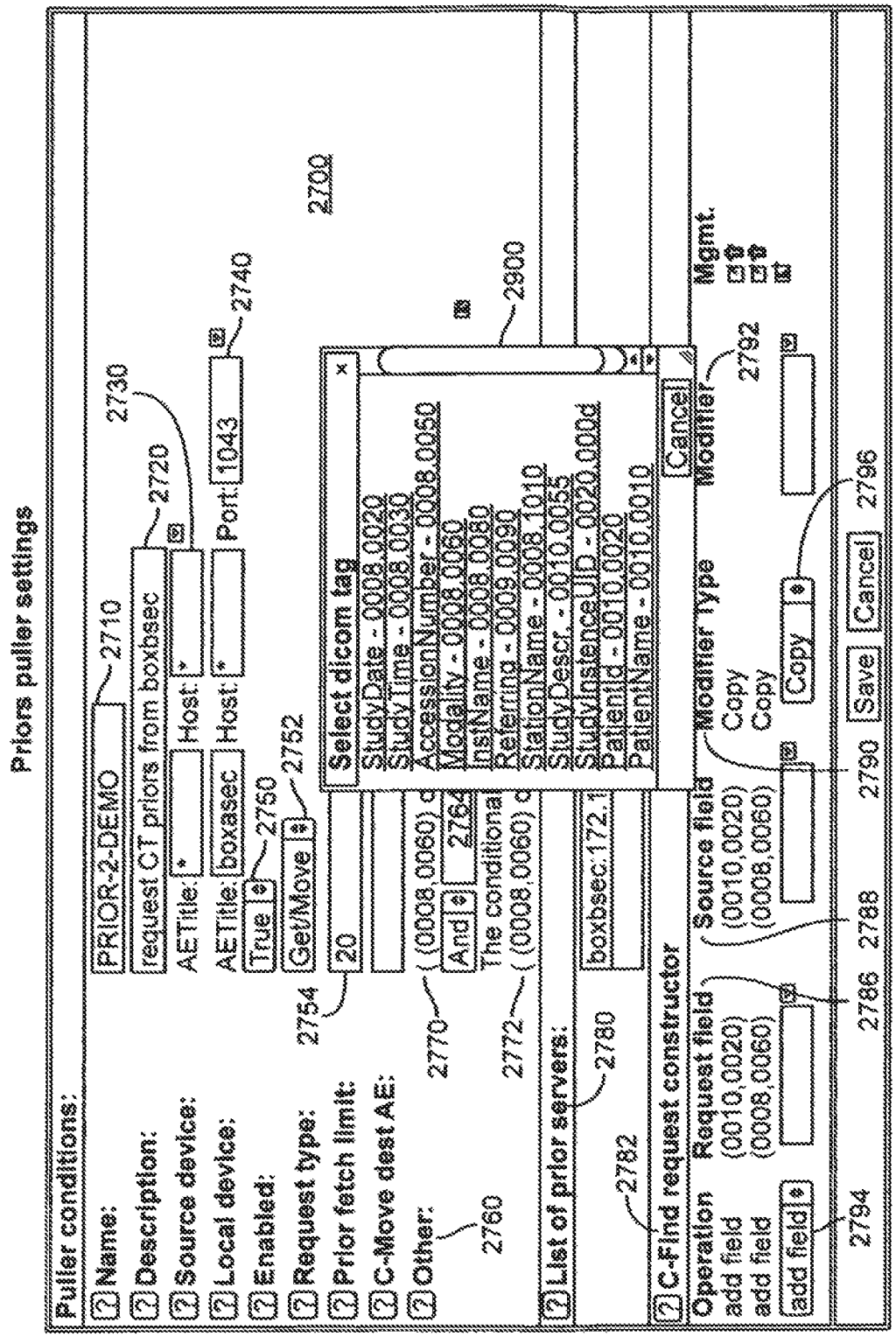
FIG. 29 is a screenshot of the graphical user interface of FIG. 25 showing a pop-up box of user-selectable DICOM tags, in accordance with one or more implementations.
Figure 30:
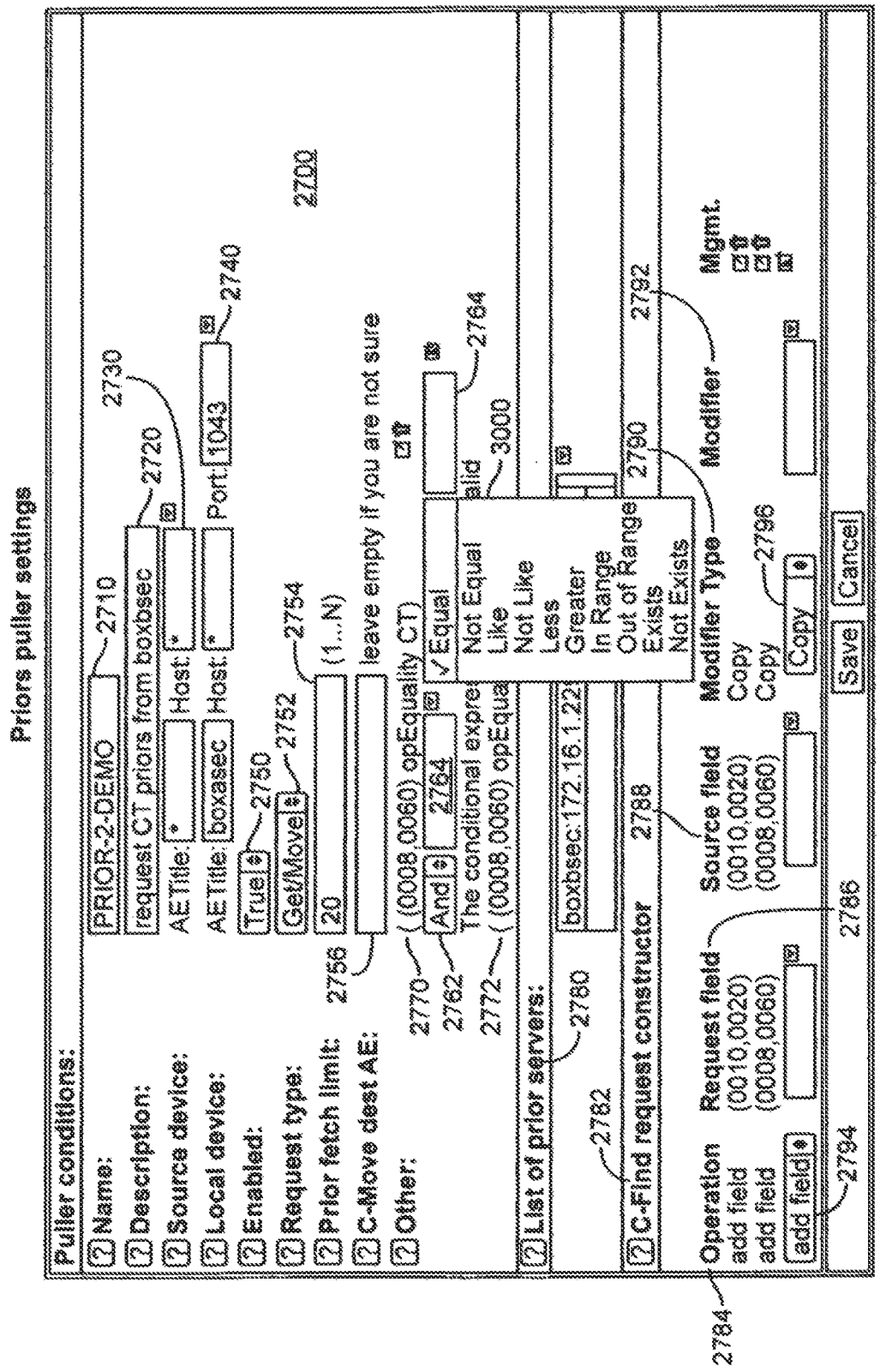
FIG. 30 is a screenshot of the graphical user interface of FIG. 25 showing a pop-up box of user-selectable conditions, in accordance with one or more implementations.

A conditional expression 2770 is user-configurable using the Other field 2760. The logical operator field 2762 (And or Or), the operands fields 2764 and the operator field 2766 provide the user with means for constructing the conditional expression 2770. As shown in FIG. 29, a pop-up box 2900 provides the user with selectable DICOM tags including user-customizable tags such as the CUSTOM TAG. With reference to FIG. 30, a pop-up box 3000 provides the user with selectable operators including Equal, Not Equal, Like, Not Like, Less, Greater, In Range, Out of Range, Exists and Not Exists. The radiological data priors puller sub-engine 600 is operable to provide the user with a confirmation 2772 of the syntax of the conditional expression 2770.

Figure 28:
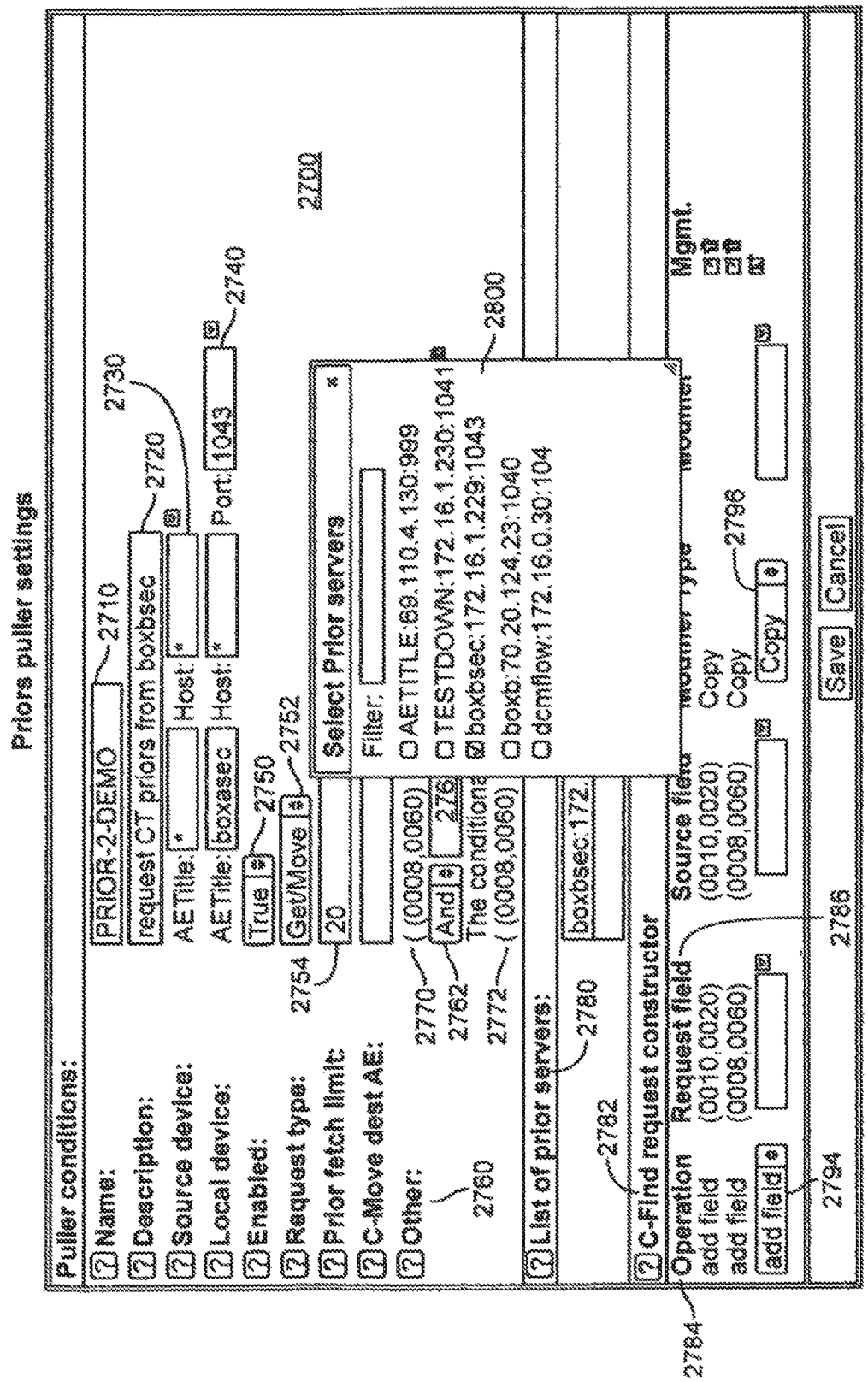
FIG. 28 is a screenshot of the graphical user interface of FIG. 25 showing a pop-up box of user-selectable prior servers, in accordance with one or more implementations.
Figure 31:
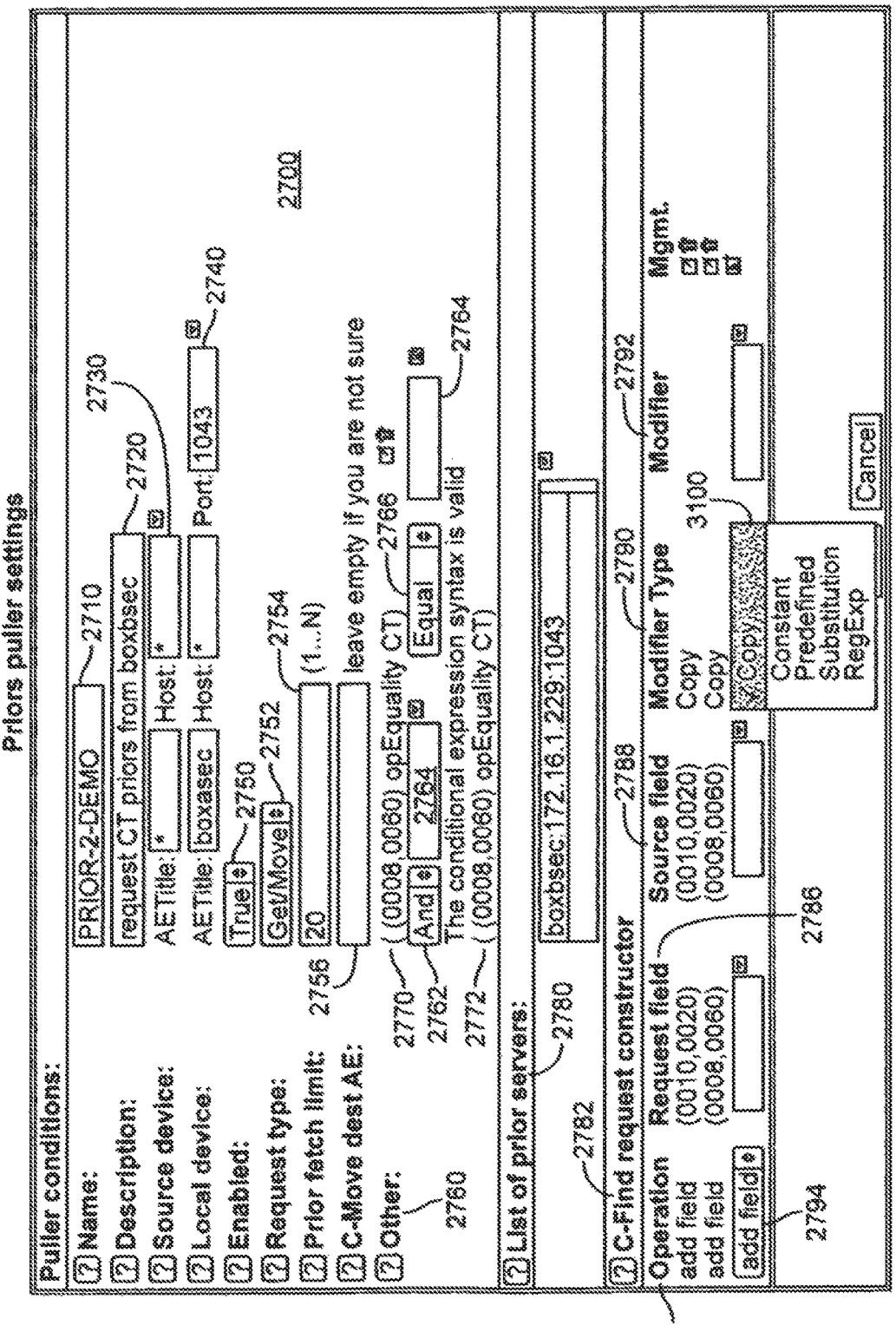
FIG. 31 is a screenshot of the graphical user interface of FIG. 25 showing a pop-up box of user-selectable modifier types, in accordance with one or more implementations.

A List of prior servers field 2780 is user-selectable by means of a pop-up box 2800 (FIG. 28). A C-Find request constructor field 2782 provides the user with configurable fields including an Operation field 2784 having a pop-up box 2794, a Request field 2786, a Source field 2788, a Modifier Type 2790 having a pop-up box 3100 (FIG. 31) and a Modifier field 2792. The Modifier Type pop-up box 3100 provides for user-selectable modifier types including Copy, Constant, Predefined, Substitution and RegExp.

In accordance with an aspect of the invention, the radiological data transformation sub-engine 300, the radiological data routing sub-engine 400, the radiological data archiving sub-engine 500 and the radiological data priors pulling sub-engine 600 can be integrated into an HL7 Workflow.

Figure 8C:
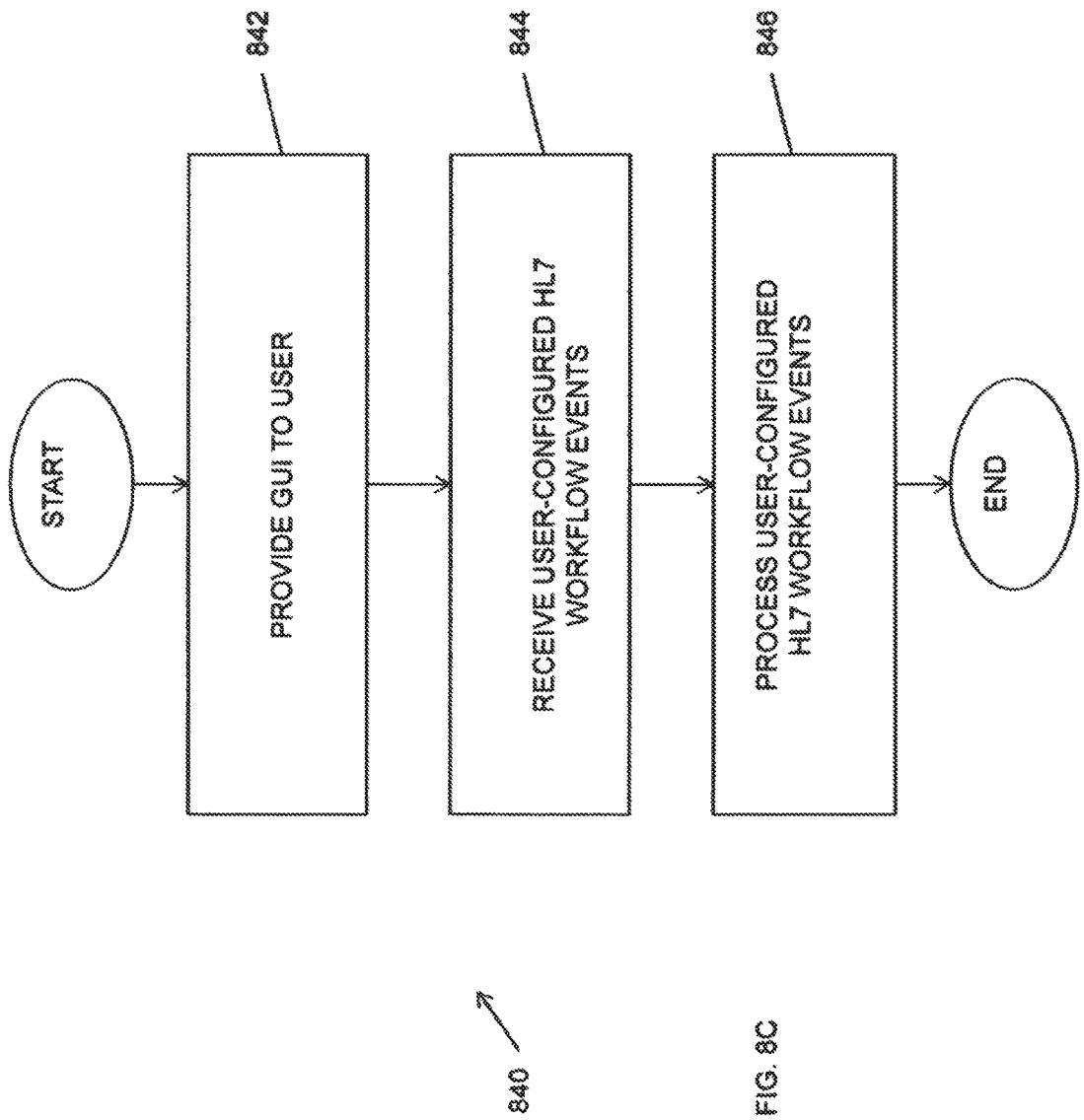
FIG. 8C is a flowchart of a computer-implemented method of providing user-configurable HL7 workflow events, in accordance with one or more implementations.

A computer-implemented method 840 (FIG. 8C) in accordance with the invention includes the steps of providing 842 a graphical user interface to the user, receiving 844 user-configured HL7 workflow events, and processing 846 the user-configured HL7 workflow events in a processor to provide for standardized HL7 workflow.

Figure 32:
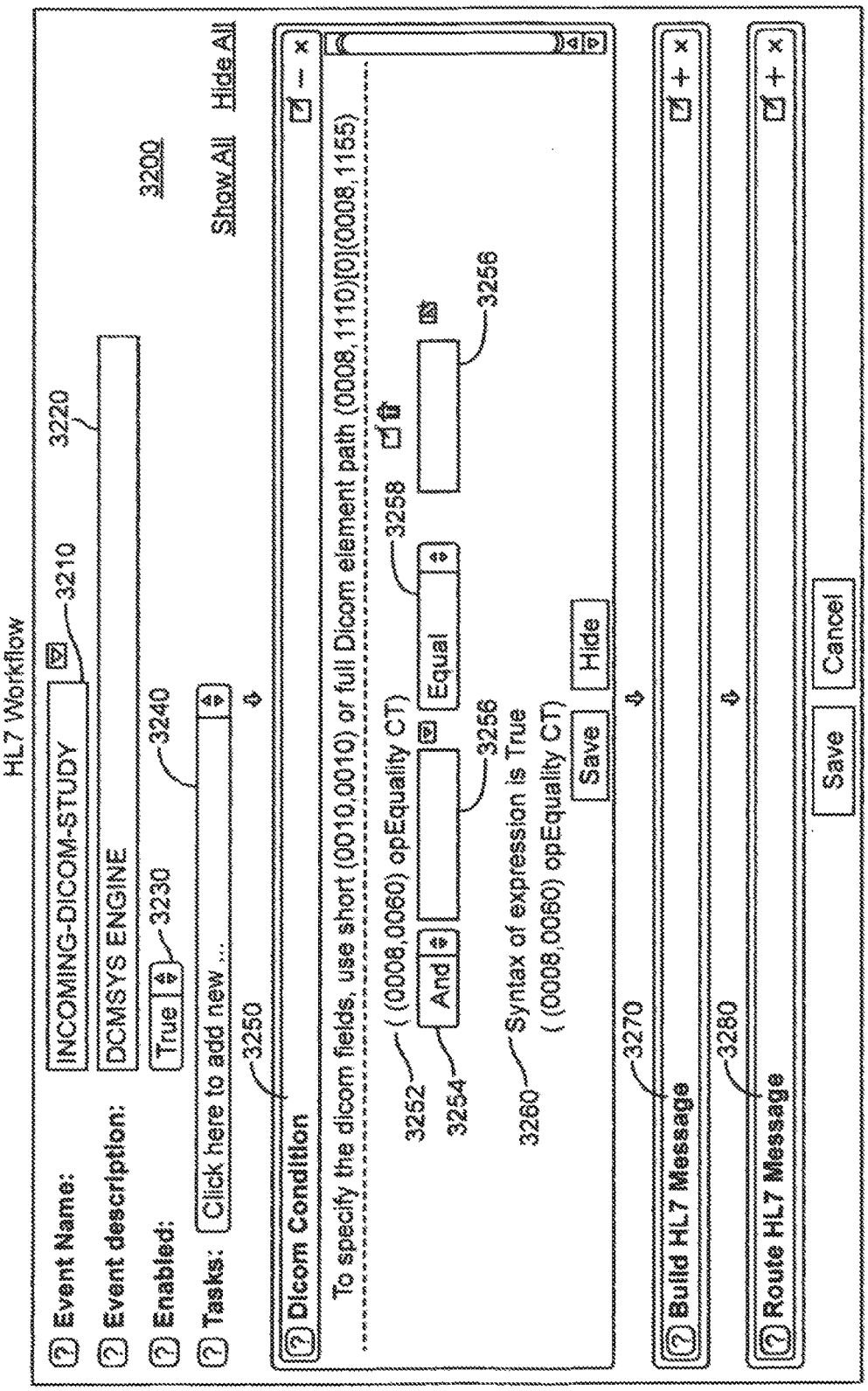
FIG. 32 is a screenshot of a graphical user interface that provides for user-configurable HL7 workflow showing a pop-up box of default events, in accordance with one or more implementations.
Figure 33:
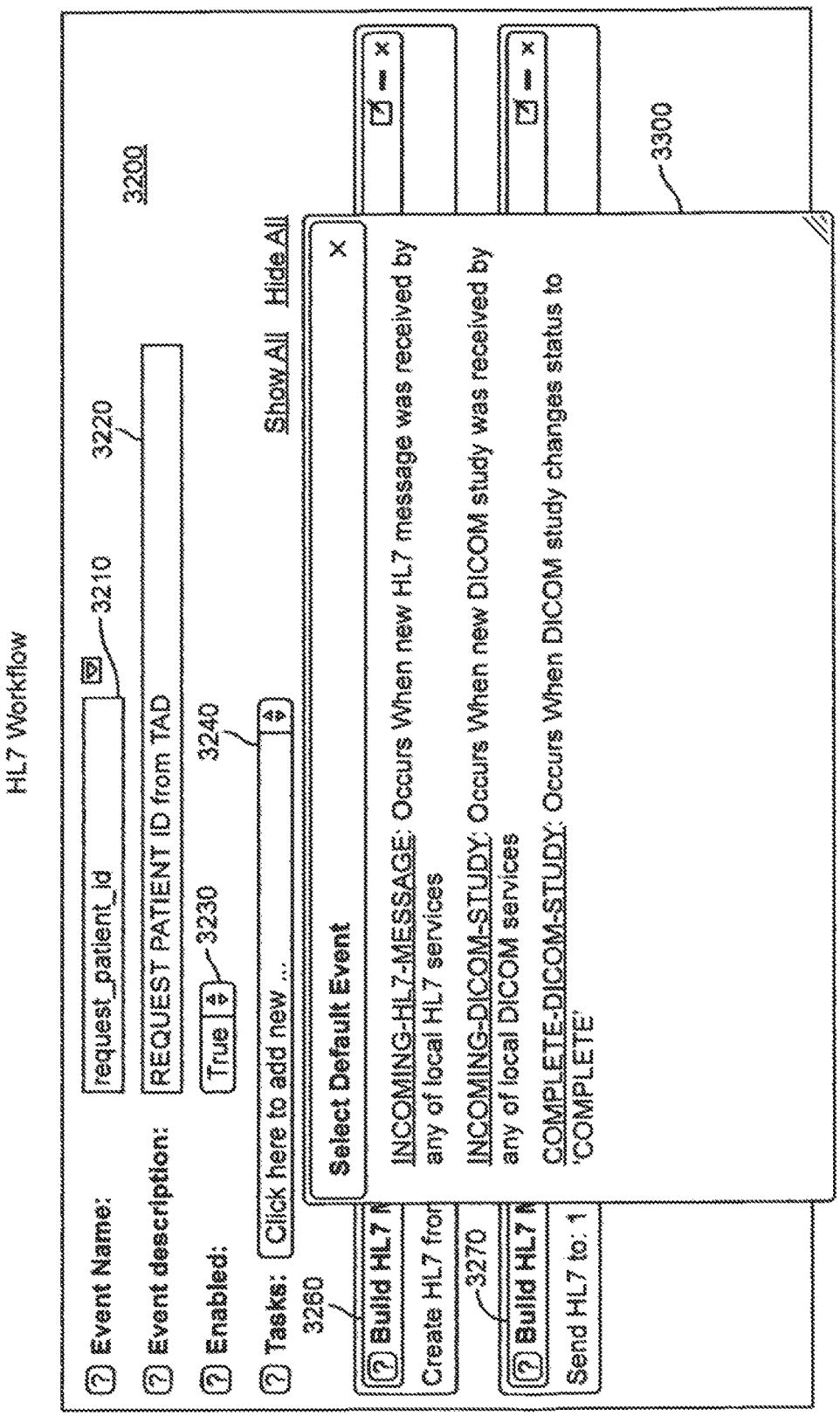
FIG. 33 is a screenshot of the graphical user interface of FIG. 32 showing DICOM conditions, in accordance with one or more implementations.

An HL7 Workflow GUI 3200 is shown in FIG. 32. The GUI 3200 provides for user-configurable events and includes an Event Name field 3210 and an Event description field 3220. A pop-up window 3300 (FIG. 33) provides for user-selectable default events such as INCOMING-HL7-MESSAGE, INCOMING-DICOM-STUDY and COMPLETE-DICOM-STUDY. The HL7 workflow may be enabled (True) or disabled (False) using the Enabled field 3230. A Dicom condition includes user-configurable fields including a logical operator field 3254 (And and Or), operand fields 3256 and an operator field 3258. For ease of use, the user is provided a confirmation 3260 of the syntax of the Dicom condition.

Figure 37:
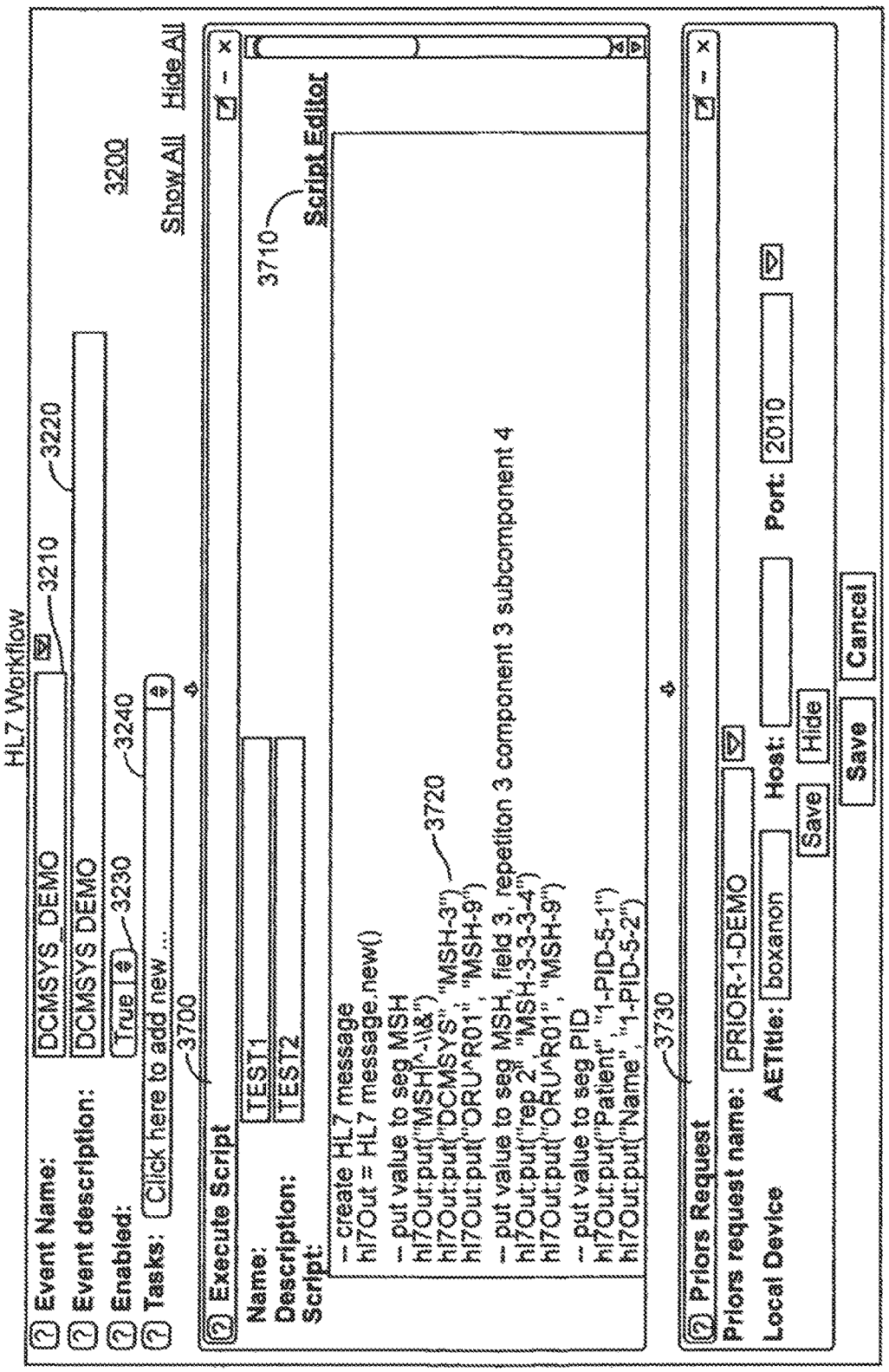
FIG. 37 is a screenshot of the graphical user interface of FIG. 32 showing a script editor, in accordance with one or more implementations.

A Tasks field 3240 includes a pop-up window 3500 (FIG. 35) from which the user may select from HL7 Condition, HL7 Transformation, Route HL7 Message, Send HL7 Message, Build Worklist entry, Export to CSV file, Build HL7 Message, Return HL7 result, Priors Request, Submit document to the XDS Repository Service, Execute script, Build Dicom object and Dicom Condition. As shown in FIG. 34, the Dicom Condition 3250, the Build HL7 Message 3260 and the Route HL7 Message 3270 tasks are selected and comprise the event "DCMSYS ENGINE". The event "DCMSYS ENGINE" also includes the HL7 Message 3270 as shown in FIG. 37. The script 3260 of the HL7 Message 3270 may be written using the HL7 Editor 3600.

With reference to FIG. 37, the event "DCMSYS DEMO" is shown and includes an Execute script event 3700 comprising the script 3720 and a Priors request 3730. The Priors request references the PRIOR-1-DEMO. The event "DCMSYS DEMO" comprises the source value 946 of the exemplary DICOM Transformation shown in FIG. 19.

With reference to FIG. 37, the event "DCMSYS DEMO" is shown and includes an Execute script event 3700 comprising the script 3720 and a Priors request 3730. The Priors request references the PRIOR-1-DEMO. The event "DCMSYS DEMO" comprises the source value 946 of the exemplary DICOM Transformation shown in FIG. 19.

A computer-implemented method 850 (FIG. 8D) in accordance with the invention includes the steps of providing 852 a graphical user interface to the user, receiving 854 a user-configured encryption scheme, and processing 856 the user-configured encryption scheme in a processor to provide for secure connection between devices.

Figure 40:
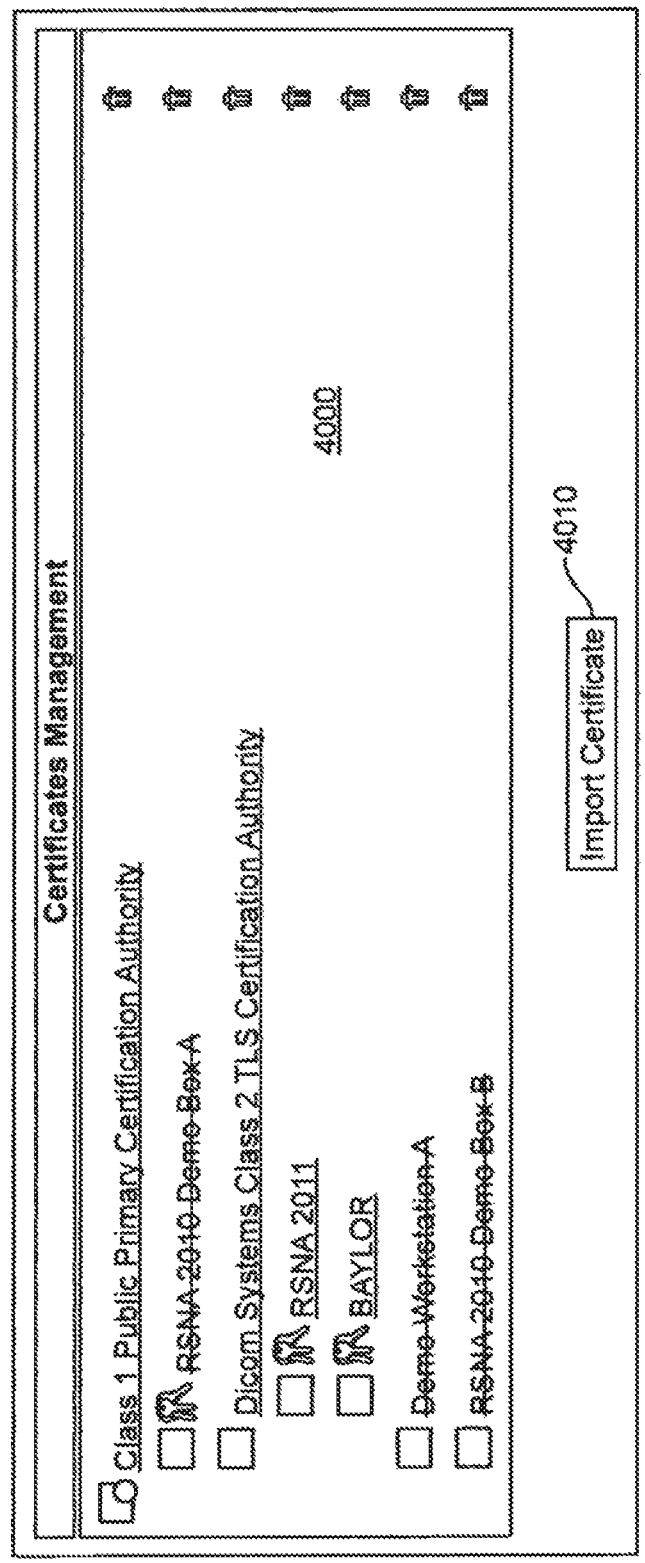
FIG. 40 is a screenshot of a graphical user interface that provides for user-configurable certificate management, in accordance with one or more implementations.
Figure 41:
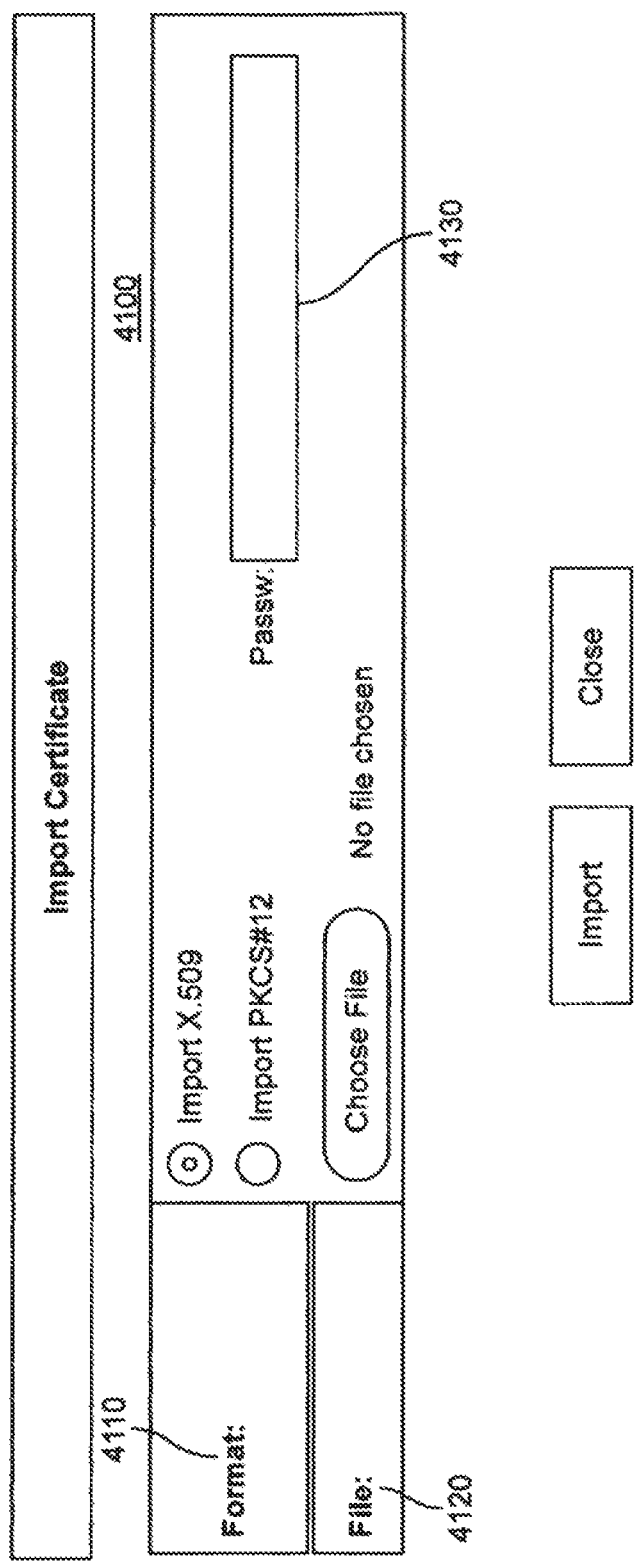
FIG. 41 is a screenshot of a graphical user that provides for user-configurable certificate importation, in accordance with one or more implementations.

To provide for user configuration and programming of the encryption scheme, a graphical user interface (GUI) 3800 is provided as shown in FIG. 38. In configuring the remote AETitle 3810, for example, a connection secure mode 3820 may be set to either Nonsecure or Secure. A local certificate 3830 and a remote trusted certificate 3840 may be selected from a pop-up window 3900 (FIG. 39). Certificate management is provided by means of a graphical user interface 4000 (FIG. 40) that includes an "Import certificate" button 4010. Certificates may be imported to the GUI 4000 and to the pop-up window 3900 by user access to the "Import Certificate" graphical user interface 4100 (FIG. 41). The format 4110 of the certificate, a password 4130 and the certificate file 4120 may be selected by means of the GUI 4100.

Figure 8E:
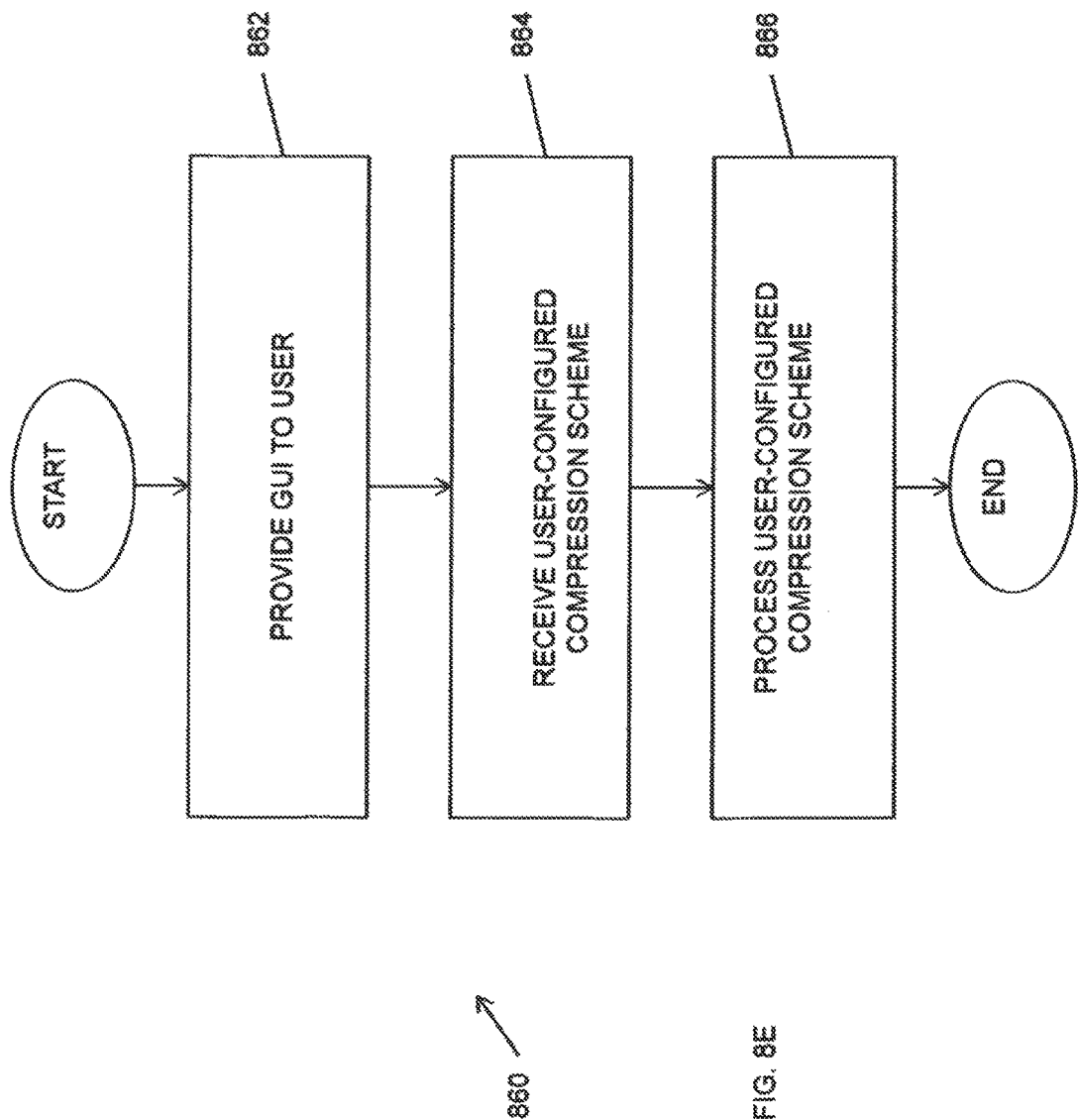
FIG. 8E is a flowchart of a computer-implemented method of providing a user-configurable data compression scheme, in accordance with one or more implementations.

A computer-implemented method 860 (FIG. 8E) in accordance with the invention includes the steps of providing 862 a graphical user interface to the user, receiving 864 a user-configured compression scheme, and processing 866 the user-configured compression scheme in a processor to provide for compression of patient radiological data.

With reference to FIG. 38, allowed incoming syntaxes 3860 and preferred outgoing syntaxes 3870 (compression schemes) are user-configurable. Transfer syntaxes selectable by the user are shown in the graphical user interfaces 4200 of FIG. 42, FIG. 43, FIG. 44 and FIG. 45.

The user-configurable radiological data transformation, routing and archiving engine in accordance with the invention provides a web-based software tool configured to run on a server or virtual base server. Users do not need to be programmers in order to write the described rules, conditions and events as the graphical user interfaces are intuitive and easy to use. The user-configurable radiological data transformation, routing and archiving engine also provides a versatile tool that provides a user with the means for transforming, routing, archiving, pulling, encrypting and compressing patient radiological data, creating worklists and managing workflow. The user-configurable radiological data transformation, routing and archiving engine further provides for the integration of the output of diverse devices in a single engine.

Figure 46:
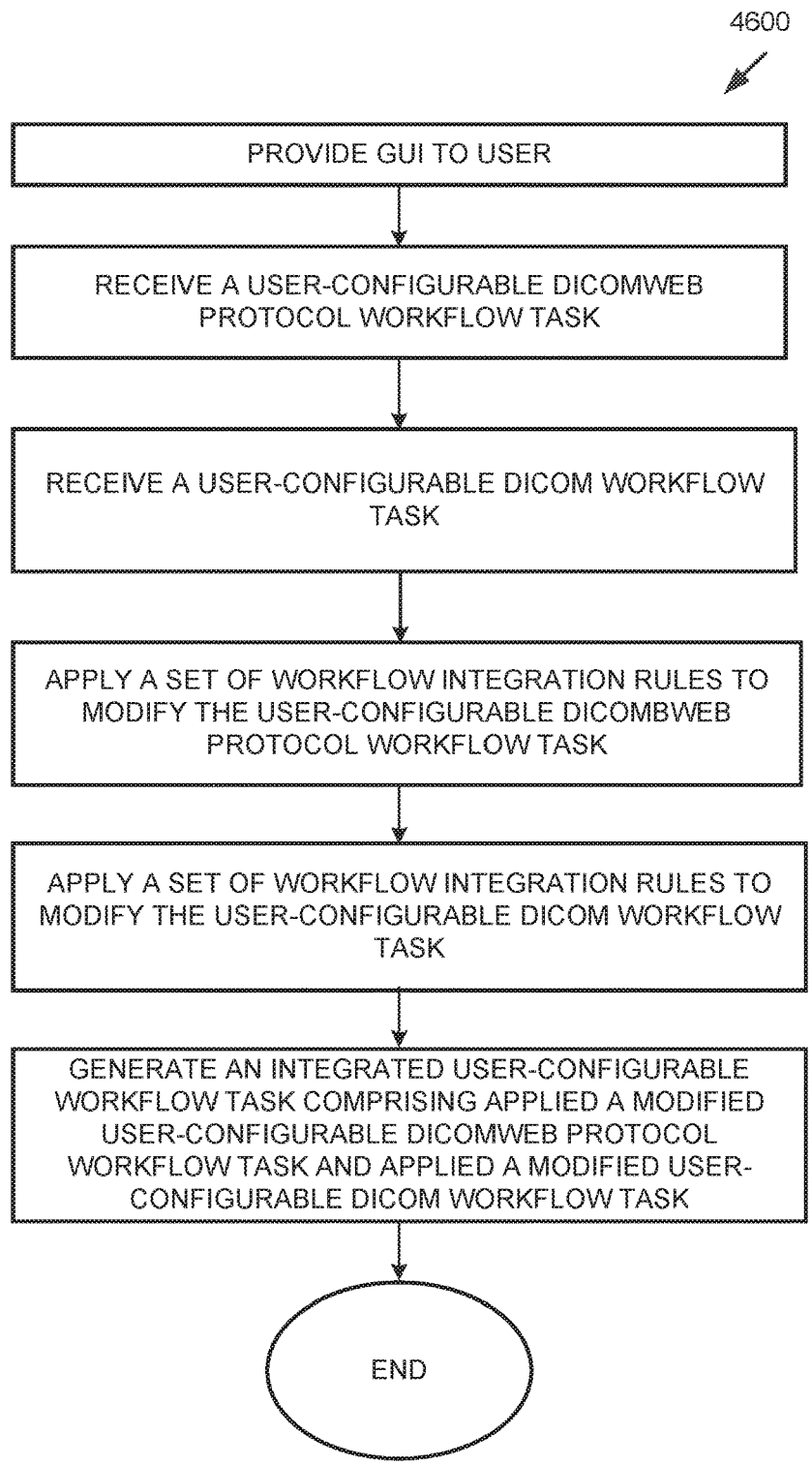
FIG. 46 is a flowchart of a computer-implemented method of integration user-configurable workflow tasks from the plurality of medical data capturing systems, in accordance with one or more implementations.

With reference to FIG. 46, it illustrates integration of user-configurable workflow tasks, consistent with embodiments disclosed herein. For example, a DICOMWEB protocol workflow task obtained a DICOMWEB protocol may be integrated with a standard DICOM user-configurable workflow task. The integration of two workflow tasks from different protocols allows users to obtain as single user-configured workflow task incorporating data from a plurality of medical data capturing systems.

As used herein, the term component might describe a given unit of functionality that can be performed in accordance with one or more embodiments of the technology disclosed herein. As used herein, a component might be implemented utilizing any form of hardware, software, or a combination thereof. For example, one or more processors, controllers, ASICs, PLAs, PALs, CPLDs, FPGAs, logical components, software routines or other mechanisms might be implemented to make up a component. In implementation, the various components described herein might be implemented as discrete components or the functions and features described can be shared in part or in total among one or more components. In other words, as would be apparent to one of ordinary skill in the art after reading this description, the various features and functionality described herein may be implemented in any given application and can be implemented in one or more separate or shared components in various combinations and permutations. As used herein, the term engine may describe a collection of components configured to perform one or more specific tasks. Even though various features or elements of functionality may be individually described or claimed as separate components or engines, one of ordinary skill in the art will understand that these features and functionality can be shared among one or more common software and hardware elements, and such description shall not require or imply that separate hardware or software components are used to implement such features or functionality.

Where engines, components, or components of the technology are implemented in whole or in part using software, in one embodiment, these software elements can be implemented to operate with a computing or processing component capable of carrying out the functionality described with respect thereto. One such example computing component is shown in FIG. 10. Various embodiments are described in terms of this example-computing component 1000. After reading this description, it will become apparent to a person skilled in the relevant art how to implement the technology using other computing components or architectures.

While various embodiments of the disclosed technology have been described above, it should be understood that they have been presented by way of example only, and not of limitation. Likewise, the various diagrams may depict an example architectural or other configuration for the disclosed technology, which is done to aid in understanding the features and functionality that can be included in the disclosed technology. The disclosed technology is not restricted to the illustrated example architectures or configurations, but the desired features can be implemented using a variety of alternative architectures and configurations. Indeed, it will be apparent to one of skill in the art how alternative functional, logical or physical partitioning and configurations can be implemented to implement the desired features of the technology disclosed herein. Also, a multitude of different constituent component names other than those depicted herein can be applied to the various partitions. Additionally, with regard to flow diagrams, operational descriptions and method claims, the order in which the steps are presented herein shall not mandate that various embodiments be implemented to perform the recited functionality in the same order unless the context dictates otherwise.

Although the disclosed technology is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the disclosed technology, whether or not such embodiments are described and whether or not such features are presented as being a part of a described embodiment. Thus, the breadth and scope of the technology disclosed herein should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent. The use of the term "component" does not imply that the components or functionality described or claimed as part of the component are all configured in a common package. Indeed, any or all of the various components of a component, whether control logic or other components, can be combined in a single package or separately maintained and can further be distributed in multiple groupings or packages or across multiple locations.

Additionally, the various embodiments set forth herein are described in terms of exemplary block diagrams, flow charts and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular architecture or configuration.

What is claimed is:

1. A user-configurable medical data filtering, transformation, integration, routing and archiving engine comprising:
a network interface coupled to a plurality of medical data capturing systems;
a medical data processing device coupled to a memory, the processing device being programmed to perform the steps of:
displaying a user interface, the user interface enabling configuration of a set of medical data filter conditions, a set of medical data transformation rules, a set of workflow integration rules, a set of routing rules, and a set of archiving rules;
wherein the set of workflow integration rules comprises a workflow integration condition, the workflow integration condition comprising a first logical operator and any of a first DICOM workflow field, a first HL7 workflow field, a first XDS-I workflow information field, a DICOMWEB protocol workflow field, and a first FHIR protocol workflow field; and
receiving, through the user interface, the set of medical data filter conditions, the set of medical data transformation rules, the set of workflow integration rules, the set of routing rules, and the set of archiving rules;
obtaining a first medical data set from the plurality of medical data capturing systems by applying the set of medical data filter conditions to the medical data capturing system;
receiving through the user interface a first user-configurable workflow task from the plurality of medical data capturing systems;
applying the set of workflow integration rules to the first user-configurable workflow task;
modifying the first user-configurable workflow task in accordance with the set of workflow integration rules when the workflow integration condition is satisfied;
obtaining a second user-configurable workflow task comprising the modified first user-configurable workflow task;
applying the second user-configurable workflow task to the first medical data set; and
modifying the first medical data set in accordance with the second user-configurable workflow task.

2. The engine of claim 1, wherein the set of medical data filter conditions comprises a first logical operator and any of a first DICOM field, a first HL7 field, a first XDS-I information field, a first DICOMWEB protocol field, a first FHIR protocol filed; and
the set of medical data transformation rules comprises a transformation filter condition, the transformation filter condition comprising a first logical operator and any of a first DICOM field, a first HL7 field, and a first XDS-I information field, a first DICOMWEB protocol field, a first FHIR protocol filed.

3. The engine of claim 2, further comprising:
modifying the first medical data set in accordance with the set of medical data transformation rules when the transformation filter condition is satisfied; and
obtaining a second medical data set comprising applied a modified first medical data set.

4. The engine of claim 1, wherein the medical data processing device is programmed to receive a user-configurable encryption scheme and a user-configurable compression scheme through the user interface and to modify medical data in accordance with the encryption scheme and the user-configurable compression scheme.

5. The engine of claim 1, wherein set of medical data transformation rules further comprises an operation selected from the group consisting of: modify field, remove field and run script.

6. The engine of claim 1, wherein the medical data processing device is further programmed to perform the step of: receiving, through the user interface priors pulling conditions, the priors pulling conditions comprising a second logical operator and any of the first DICOM field, a second DICOM field, the first HL7 field, a second HL7 field, the first XDS-I information field, and a second XDS-I information field, the first DICOMWEB protocol field, a second DICOMWEB protocol field, the first FHIR protocol field, and a second FHIR protocol field.

7. The engine of claim 1, wherein the workflow integration condition of the set of workflow integration rules further comprises a task selected from the group consisting of HL7 condition, HL7 transformation, route HL7 message, send HL7 message, build HL7 worklist entry, export to CSV file, build HL7 message, return HL7 message, priors request, submit document to the XDS repository service, execute script, build DICOM object and DICOM condition.

8. The engine of claim 1, wherein the workflow integration condition of the set of workflow integration rules further comprises a task selected from the group consisting of FHIR condition, FHIR transformation, route FHIR message, send FHIR message, build a FHIR worklist entry, export to CSV file, build FHIR message, return FHIR message, priors request, submit document to the XDS repository service, execute script, build DICOM object and DICOM condition.

9. The engine of claim 1, wherein:
the set of routing rules comprises a routing condition, the routing condition comprising a second logical operator and any of the first DICOM field, a second DICOM field tags, the first HL7 field, a second HL7 field, the first XDS-I information filed, and a second XDS-I information field, the first DICOMWEB protocol field, a second DICOMWEB protocol field, the first FHIR protocol field, and a second FHIR protocol field; and
the medical data processing device is further configured to perform the step of routing the medical data in accordance with the set of routing rules if the routing filter condition is satisfied.

10. The engine of claim 1, wherein:
the set of archiving rules comprises an archiving condition, the archiving condition comprising a second logical operator and any of the first DICOM field, a second DICOM field, the first HL7 field, a second HL7 field, a third HL7 field, the first XDS-I information field, and a second XDS-I information field, the first DICOMWEB protocol field, a second DICOMWEB protocol field, the first FHIR protocol field, and a second FHIR protocol field; and
the medical data processing device is further configured to perform the step of archiving the medical data in accordance with the set of archiving rules if the archiving filter condition is satisfied.

11. A computer-implemented method of filtering, transforming, integrating, routing and archiving radiological data comprising:
providing, from a medical data processing device coupled to a memory, a graphical user interface (GUI) coupled to a plurality of medical data capturing systems, the GUI enabling configuration of a set of medical data filter conditions, a set of medical data transformation rules, a set of routing conditions, a set of routing rules, a set of priors pulling conditions, a set of priors pulling rules, a set of workflow integration rules, a set of archiving conditions, and a set of archiving rules;
wherein the set of workflow integration rules comprises a workflow integration condition, the workflow integration condition comprising a first logical operator and any of a first DICOM workflow field, a first HL7 workflow field, a first XDS-I workflow information field, a first DICOMWEB protocol workflow field, and a first FHIR protocol workflow field; and
receiving, at the medical data processing device, the set of medical data filter conditions, the set of medical data transformation rules, the set of predetermined modification parameters, the set of routing conditions, the set of routing rules, the set of priors pulling conditions, the set of priors pulling rules, the set of workflow integration rules, the set of archiving conditions, and the set of archiving rules;
obtaining a first medical data set from the plurality of medical data capturing systems;
executing, with the medical data processing device, the user-configurable script when the set of medical data filter conditions are satisfied;
receiving through the user interface a first user-configurable workflow task from the plurality of medical data capturing systems;
applying the set of workflow integration rules to the first user-configurable workflow task;
modifying the first user-configurable workflow task in accordance with the set of workflow integration rules when the workflow integration condition is satisfied; and
obtaining a second user-configurable workflow task comprising the modified first user-configurable workflow task;
applying the second user-configurable workflow task to the first medical data set; and
modifying the first medical data set in accordance with the second user-configurable workflow task.

12. The computer-implemented method of claim 11, wherein the set of medical data filter conditions comprises a first logical operator and any of a first DICOM field, a first HL7 field, a first XDS-I information field, a first DICOMWEB protocol field, and a first FHIR protocol field; and
the set of medical data transformation rules comprises a user-configurable script configured to cause the medical data processing device to modify a set of medical data in accordance with a set of predetermined modification parameters.

13. The computer-implemented method of claim 12, further comprising
modifying the first medical data set in accordance with the set of medical data transformation rules when the transformation filter condition is satisfied; and
obtaining a second medical data set comprising a modified first medical data set.

14. The computer-implemented method of claim 11, further comprising receiving, at the medical data processing device, a user-configurable encryption scheme and a user-configurable compression scheme.

15. The computer-implemented method of claim 11, wherein, the set of routing rules comprises a second logical operator and any of the first DICOM field, a second DICOM field, the first HL7 field, a second HL7 field, the first XDS-I information field, and a second XDS-I information field, the first DICOMWEB protocol field, a second DICOMWEB protocol field, the first FHIR protocol field, and a second FHIR protocol field.

16. The computer-implemented method of claim 11, wherein the set of priors pulling conditions comprises a second logical operator and any of the first DICOM field, a second DICOM field, the first HL7 field, a second HL7 field, the first XDS-I information field, and a second XDS-I information field, the first DICOMWEB protocol field, a second DICOMWEB protocol field, the first FHIR protocol field, and a second FHIR protocol field.

17. The computer-implemented method of claim 11, wherein the set of archiving rules comprises user-configurable storage duration.

18. The computer-implemented method of claim 11, wherein the workflow integration condition of the set of the workflow integration rules comprises a second logical operator and any of a first FHIR protocol request, a second FHIR protocol request, a first DICOMWEB protocol request, and a second DICOMWEB protocol request.

19. The computer-implemented method of claim 18, wherein the first DICOMWEB protocol request is integrated with a first DICOM request.

20. The computer-implemented method of claim 18, wherein the first FHIR protocol request is integrated with a first HL7 request.

\* \* \* \* \*